US009360485B2

(12) United States Patent
Yeh et al.

(10) Patent No.: US 9,360,485 B2
(45) Date of Patent: *Jun. 7, 2016

(54) EUKARYOTIC EXPRESSION SYSTEM AND USE THEREOF

(71) Applicant: National Chung Hsing University, Taichung (TW)

(72) Inventors: Shyi-Dong Yeh, Taichung (TW); Hao-Wen Cheng, Taichung (TW)

(73) Assignee: National Chung Hsing University, Taichung (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/070,850

(22) Filed: Nov. 4, 2013

(65) Prior Publication Data

US 2015/0125849 A1  May 7, 2015

(51) Int. Cl.
| | |
|---|---|
| C12Q 1/70 | (2006.01) |
| C12N 5/04 | (2006.01) |
| G01N 33/68 | (2006.01) |
| C12N 15/62 | (2006.01) |
| C12N 15/82 | (2006.01) |

(52) U.S. Cl.
CPC ............ *G01N 33/6878* (2013.01); *C12N 15/62* (2013.01); *C12N 15/8257* (2013.01); *C12N 15/8258* (2013.01)

(58) Field of Classification Search
None
See application file for complete search history.

(56) References Cited

U.S. PATENT DOCUMENTS

| | | | |
|---|---|---|---|
| 7,129,060 B1 * | 10/2006 | Maurer et al. | 435/69.1 |
| 2004/0214160 A1 * | 10/2004 | Gleba et al. | 435/5 |
| 2008/0003617 A1 * | 1/2008 | Fan et al. | 435/7.1 |

OTHER PUBLICATIONS

Chen et al., "Identification of Common Epitopes on a Conserved Region of NSs Proteins Among Tospoviruses of Watermelon silver mottle virus Serogroup," Phytopathology, vol. 96, No. 12: 1296-1304 (2006).*
Voinnet et al., "An enhanced transient expression system in plants based on suppression of gene silencing by the p19 protein of tomato bushy stunt virus," The Plant Journal 33: 949-956 (2003).*
Peng et al., "Mutations in the HC-Pro gene of zucchini yellow mosaic potyvirus: effects on aphid transmission and binding to purified virions," Journal of General Virology, 79: 897-904 (1998).*

(Continued)

*Primary Examiner* — Benjamin P Blumel
*Assistant Examiner* — M. Franco Salvoza
(74) *Attorney, Agent, or Firm* — Fishman & Associates, LLC.

(57) ABSTRACT

Provided are a eukaryotic expression system and its applications. The eukaryotic expression system has a recombinant plant cell. The recombinant plant cell includes a first vector and a second vector. The first vector expresses a fusion protein containing an Asia tospoviral common epitope. The fusion protein containing Asia tospoviral common epitope consists of an amino acid sequence as set forth in SEQ ID NO. 1, and a predetermined protein fragment connecting to the Asia tospoviral common epitope. The above eukaryotic expression system is useful for monitoring the interaction between proteins via use of a specific peptide to tag the predetermined protein and demonstrates high sensitivity and stability.

12 Claims, 17 Drawing Sheets

(56) References Cited

OTHER PUBLICATIONS

Roggero et al., "Effects of temperature on infection in *Capsicum* sp. and *Nicotiana benthamiana* by impatiens necrotic spot tospovirus," European Journal of Plant Pathology, 105: 509-512 (1999).*

Cheng et al., "An efficient tag derived from the common epitope of tospoviral NSs proteins for monitoring recombinant proteins expressed in both bacterial and plant systems," Journal of Biotechnology 164: 510-519 (2013).*

Lin et al., "RING1 E3 ligase localizes to plasma membrane lipid rafts to trigger FB1-induced programmed cell death in Arabidopsis," The Plant Journal, 56: 550-561 (2008).*

* cited by examiner

SEQUENCE LISTING

<160> NUMBER OF SEQ ID NOS: 57

<210> SEQ ID NO 1
<211> LENGTH: 9
<212> TYPE: PRT
<213> ORGANISM: Watermelon silver mottle virus
<220> FEATURE:
<221> NAME/KEY: SOURCE
<222> LOCATION: 1..9
<223> OTHER INFORMATION: /mol_type="protein"
　　　　/organism="Watermelon silver mottle virus"

<400> SEQUENCE: 1

Lys Phe Thr Met His Asn Gln Ile Phe
1               5

<210> SEQ ID NO 2
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
　　　　/note="P-PCAA-GFP"
　　　　/organism="artificial sequences"

<400> SEQUENCE: 2
caccatggtg agcaagggcg aggagct                                         27

<210> SEQ ID NO 3
<211> LENGTH: 58
<212> TYPE: DNA
<213> ORGANISM: artificial sequences
<220> FEATURE:
<221> NAME/KEY: source
<222> LOCATION: 1..58
<223> OTHER INFORMATION: /mol_type="DNA"
　　　　/note="M-NSsconG1BK"
　　　　/organism="artificial sequences"

<400> SEQUENCE: 3
gttcttcaca cctggtttcc ttacggtacc ggatcccttg tacagctcgt ccatgccg     58

<210> SEQ ID NO 4
<211> LENGTH: 49
<212> TYPE: DNA
<213> ORGANISM: artificial sequences
<220> FEATURE:
<221> NAME/KEY: source
<222> LOCATION: 1..49
<223> OTHER INFORMATION: /mol_type="DNA"
　　　　/note="M-NSsconG2"
　　　　/organism="artificial sequences"

<400> SEQUENCE: 4
ttgattgtgc attgtgaact tgcagcctgt gttcttcaca cctggtttc               49

<210> SEQ ID NO 5
<211> LENGTH: 43
<212> TYPE: DNA
<213> ORGANISM: artificial sequences
<220> FEATURE:
<221> NAME/KEY: source
<222> LOCATION: 1..43
<223> OTHER INFORMATION: /mol_type="DNA"
　　　　/note="M-NSscon"
　　　　/organism="artificial sequences"

<400> SEQUENCE: 5
ggtgctcgag atttggatta aagatttgat tgtgcattgt gaa        43

<210> SEQ ID NO 6
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="M-pET28-XmaI"
      /organism="artificial sequences"

<400> SEQUENCE: 6
gcatggttac tcaccactgc g        21

<210> SEQ ID NO 7
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="P-NSscon-d2"
      /organism="artificial sequences"

<400> SEQUENCE: 7
gtggtaccaa accaggtgtg aagaacac        28

<210> SEQ ID NO 8
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d4"
      /organism="artificial sequences"

<400> SEQUENCE: 8
gtggtaccgg tgtgaagaac acaggctgc        29

<210> SEQ ID NO 9
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d6"
      /organism="artificial sequences"

<400> SEQUENCE: 9
gtggtaccaa gaacacaggc tgcaagttc        29

<210> SEQ ID NO 10
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d8"
      /organism="artificial sequences"

```
<400> SEQUENCE: 10
gtggtaccac aggctgcaag ttcacaatg                                29

<210> SEQ ID NO 11
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d10"
      /organism="artificial sequences"

<400> SEQUENCE: 11
gtggtacctg caagttcaca atgcacaat                                29

<210> SEQ ID NO 12
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d11"
      /organism="artificial sequences"

<400> SEQUENCE: 12
cgtggtacca agttcacaat gcacaatca                                29

<210> SEQ ID NO 13
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="P-NSscon-d12"
      /organism="artificial sequences"

<400> SEQUENCE: 13
cgtggtacct tcacaatgca caatcaaat                                29

<210> SEQ ID NO 14
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
      /note="P-CACC-GFP"
      /organism="artificial sequences"

<400> SEQUENCE: 14
caccatggtg agcaagggcg aggagct                                  27

<210> SEQ ID NO 15
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="M-NSscon-d2"
      /organism="artificial sequences"
```

```
<400> SEQUENCE: 15
tgctcgagat taaagatttg attgtgcatt                              30

<210> SEQ ID NO 16
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="M-NSscon-d3"
      /organism="artificial sequences"

<400> SEQUENCE: 16
tgctcgagaa agatttgatt gtgcattgtg                              30

<210> SEQ ID NO 17
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="M-NSscon-d4"
      /organism="artificial sequences"

<400> SEQUENCE: 17
tgctcgagga tttgattgtg cattgtgaa                               29

<210> SEQ ID NO 18
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="M-NSscon-d5"
      /organism="artificial sequences"

<400> SEQUENCE: 18
tgctcgagtt gattgtgcat tgtgaactt                               29

<210> SEQ ID NO 19
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="M-NSscon-d6"
      /organism="artificial sequences"

<400> SEQUENCE: 19
tgctcgagat tgtgcattgt gaacttgca                               29

<210> SEQ ID NO 20
<211> LENGTH: 37
<212> TYPE: DNA
<213> ORGANISM: artificial sequences
<220> FEATURE:
<221> NAME/KEY: source
<222> LOCATION: 1..37
<223> OTHER INFORMATION: /mol_type="DNA"
      /note="P-del.SphI"
```

/organism="artificial sequences"

<400> SEQUENCE: 20
ccgccgcaag gaatggtgca aggagatggc gcccaac                              37

<210> SEQ ID NO 21
<211> LENGTH: 37
<212> TYPE: DNA
<213> ORGANISM: artificial sequences
<220> FEATURE:
<221> NAME/KEY: source
<222> LOCATION: 1..37
<223> OTHER INFORMATION: /mol_type="DNA"
      /note="M-del.SphI"
      /organism="artificial sequences"

<400> SEQUENCE: 21
gttgggcgcc atctccttgc accattcctt gcggcgg                              37

<210> SEQ ID NO 22
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="P-del.ApaI"
      /organism="artificial sequences"

<400> SEQUENCE: 22
gagacagaac ttaatggacc cgctaacagc                                      30

<210> SEQ ID NO 23
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="M-del.ApaI"
      /organism="artificial sequences"

<400> SEQUENCE: 23
gctgttagcg ggtccattaa gttctgtctc                                      30

<210> SEQ ID NO 24
<211> LENGTH: 38
<212> TYPE: DNA
<213> ORGANISM: artificial sequences
<220> FEATURE:
<221> NAME/KEY: source
<222> LOCATION: 1..38
<223> OTHER INFORMATION: /mol_type="DNA"
      /note="P-GFP-NSA"
      /organism="artificial sequences"

<400> SEQUENCE: 24
gccatggcat gcgggcccgt gagcaagggc gaggagct                             38

<210> SEQ ID NO 25
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"

/note="M-GFP-BKX"
    /organism="artificial sequences"

<400> SEQUENCE: 25
ggtgctcgag ggtaccggat cccttgtaca gctcgtccat          40

<210> SEQ ID NO 26
<211> LENGTH: 43
<212> TYPE: DNA
<213> ORGANISM: artificial sequences
<220> FEATURE:
<221> NAME/KEY: source
<222> LOCATION: 1..43
<223> OTHER INFORMATION: /mol_type="DNA"
    /note="M-GFP-TGA"
    /organism="artificial sequences"

<400> SEQUENCE: 26
ggtgctcgag tcaggtaccg gatcccttgt acagctcgtc cat          43

<210> SEQ ID NO 27
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
    /note="M-NSsconTGA"
    /organism="artificial sequences"

<400> SEQUENCE: 27
gcctcgagtc aatttggatt aaagatttga ttgtg          35

<210> SEQ ID NO 28
<211> LENGTH: 54
<212> TYPE: DNA
<213> ORGANISM: artificial sequences
<220> FEATURE:
<221> NAME/KEY: source
<222> LOCATION: 1..54
<223> OTHER INFORMATION: /mol_type="DNA"
    /note="P-NSscon1"
    /organism="artificial sequences"

<400> SEQUENCE: 28
ttcacaatgc acaatcaaat ctttaatcca aatgccatgg catgcgggcc cgtg          54

<210> SEQ ID NO 29
<211> LENGTH: 54
<212> TYPE: DNA
<213> ORGANISM: artificial sequences
<220> FEATURE:
<221> NAME/KEY: source
<222> LOCATION: 1..54
<223> OTHER INFORMATION: /mol_type="DNA"
    /note="P-NSscon2"
    /organism="artificial sequences"

<400> SEQUENCE: 29
gtaaggaaac caggtgtgaa gaacacaggc tgcaagttca caatgcacaa tcaa          54

<210> SEQ ID NO 30
<211> LENGTH: 33
<212> TYPE: DNA
<213> ORGANISM: artificial sequences
<220> FEATURE:
<221> NAME/KEY: source
<222> LOCATION: 1..33

```
<223> OTHER INFORMATION: /mol_type="DNA"
     /note="P-NSscon"
     /organism="artificial sequences"

<400> SEQUENCE: 30
caccacatgt ccgtaaggaa accaggtgtg aag                                   33

<210> SEQ ID NO 31
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
     /note="P-Cnss"
     /organism="artificial sequences"

<400> SEQUENCE: 31
caatcaaatc ttttgagatc cggctgctaa caaa                                  34

<210> SEQ ID NO 32
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
     /note="M-Cnss"
     /organism="artificial sequences"

<400> SEQUENCE: 32
tgcattgtga acttctcgag ggtaccggat cccttg                                36

<210> SEQ ID NO 33
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
     /note="P-Nnss"
     /organism="artificial sequences"

<400> SEQUENCE: 33
acaatcaaat ctttcatgcg ggcccgtgag caagg                                 35

<210> SEQ ID NO 34
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
     /note="M-Nnss"
     /organism="artificial sequences"

<400> SEQUENCE: 34
gcattgtgaa cttcaccatg gtatatctcc ttctta                                36

<210> SEQ ID NO 35
<211> LENGTH: 30
<212> TYPE: DNA
<213> ORGANISM: artificial sequences
<220> FEATURE:
<221> NAME/KEY: source
```

```
<222> LOCATION: 1..30
<223> OTHER INFORMATION: /mol_type="DNA"
      /note="P-Nhis"
      /organism="artificial sequences"

<400> SEQUENCE: 35
caccaccacc atgcgggccc gtgagcaagg                                          30

<210> SEQ ID NO 36
<211> LENGTH: 32
<212> TYPE: DNA
<213> ORGANISM: artificial sequences
<220> FEATURE:
<221> NAME/KEY: source
<222> LOCATION: 1..32
<223> OTHER INFORMATION: /mol_type="DNA"
      /note="M-Nhis"
      /organism="artificial sequences"

<400> SEQUENCE: 36
gtgatggtgc atggtatatc tccttcttaa ag                                       32

<210> SEQ ID NO 37
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="P-WNpro"
      /organism="artificial sequences"

<400> SEQUENCE: 37
ccgcatgcgg aaaaagtctt tgccaaggca                                          30

<210> SEQ ID NO 38
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="M-WNpro"
      /organism="artificial sequences"

<400> SEQUENCE: 38
cagcatgctt gttcaaaaac attcaattga t                                        31

<210> SEQ ID NO 39
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="P-ZHC"
      /organism="artificial sequences"

<400> SEQUENCE: 39
cagcatgctc gtcgcaaccg gaagttcagt tct                                      33

<210> SEQ ID NO 40
<211> LENGTH: 35
<212> TYPE: DNA
<213> ORGANISM: artificial sequences
<220> FEATURE:
```

```
<221> NAME/KEY: source
<222> LOCATION: 1..35
<223> OTHER INFORMATION: /mol_type="DNA"
      /note="M-ZHC"
      /organism="artificial sequences"

<400> SEQUENCE: 40
caggatccgc caactctgta atgcttcatc tcgct                           35

<210> SEQ ID NO 41
<211> LENGTH: 32
<212> TYPE: DNA
<213> ORGANISM: artificial sequences
<220> FEATURE:
<221> NAME/KEY: source
<222> LOCATION: 1..32
<223> OTHER INFORMATION: /mol_type="DNA"
      /note="P-Dp25"
      /organism="artificial sequences"

<400> SEQUENCE: 41
gcgggcccga tcaagtcgat gtcaaagatt gt                              32

<210> SEQ ID NO 42
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="M-Dp25"
      /organism="artificial sequences"

<400> SEQUENCE: 42
caggatccaa cttcaatctt tttaacacgt gct                             33

<210> SEQ ID NO 43
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="P-WNP"
      /organism="artificial sequences"

<400> SEQUENCE: 43
ccgcatgcat gtctaacgtt aagcagctca caga                            34

<210> SEQ ID NO 44
<211> LENGTH: 32
<212> TYPE: DNA
<213> ORGANISM: artificial sequences
<220> FEATURE:
<221> NAME/KEY: source
<222> LOCATION: 1..32
<223> OTHER INFORMATION: /mol_type="DNA"
      /note="P-WNP"
      /organism="artificial sequences"

<400> SEQUENCE: 44
caggtaccca cttccaaaga agtgctgggc tt                              32

<210> SEQ ID NO 45
<211> LENGTH: 26
<212> TYPE: DNA
<213> ORGANISM: artificial sequences
```

```
<220> FEATURE:
<221> NAME/KEY: source
<222> LOCATION: 1..26
<223> OTHER INFORMATION: /mol_type="DNA"
      /note="P-nss-d6"
      /organism="artificial sequences"

<400> SEQUENCE: 45
aagttcacaa tgcacaatca aatctt                                          26

<210> SEQ ID NO 46
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="P-his-d6"
      /organism="artificial sequences"

<400> SEQUENCE: 46
caccaccacc accaccactg a                                               21

<210> SEQ ID NO 47
<211> LENGTH: 25
<212> TYPE: DNA
<213> ORGANISM: artificial sequences
<220> FEATURE:
<221> NAME/KEY: source
<222> LOCATION: 1..25
<223> OTHER INFORMATION: /mol_type="DNA"
      /note="M-ZHC-d6"
      /organism="artificial sequences"

<400> SEQUENCE: 47
catctcgctc tgtagatcat ttgag                                           25

<210> SEQ ID NO 48
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="P-ZCP"
      /organism="artificial sequences"

<400> SEQUENCE: 48
ccgcatgctc aggcactcag ccaactgc                                        28

<210> SEQ ID NO 49
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="M-ZCP"
      /organism="artificial sequences"

<400> SEQUENCE: 49
cagcatgcct gcattgtgtt cacacctaa                                       29

<210> SEQ ID NO 50
<211> LENGTH: 38
<212> TYPE: DNA
```

```
<213> ORGANISM: artificial sequences
<220> FEATURE:
<221> NAME/KEY: source
<222> LOCATION: 1..38
<223> OTHER INFORMATION: /mol_type="DNA"
      /note="P-ZGn"
      /organism="artificial sequences"

<400> SEQUENCE: 50
cacaatcaaa tctttctcga gtccgtacgg ctccagtc                           38

<210> SEQ ID NO 51
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="M-ZGn"
      /organism="artificial sequences"

<400> SEQUENCE: 51
cattgtgaac ttggtaccac gcgtcttgta cag                               33

<210> SEQ ID NO 52
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="P-ZnG"
      /organism="artificial sequences"

<400> SEQUENCE: 52
caatcaaatc tttgccggcg catgcgggcc cgtgag                            36

<210> SEQ ID NO 53
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="M-ZnG"
      /organism="artificial sequences"

<400> SEQUENCE: 53
tgcattgtga acttacccat ggtcgacgaa tagt                              34

<210> SEQ ID NO 54
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="P-Zdhis"
      /organism="artificial sequences"

<400> SEQUENCE: 54
ctcgagtccg tacggctcca gtcatcca                                     28

<210> SEQ ID NO 55
<211> LENGTH: 25
```

```
<212> TYPE: DNA
<213> ORGANISM: artificial sequences
<220> FEATURE:
<221> NAME/KEY: source
<222> LOCATION: 1..25
<223> OTHER INFORMATION: /mol_type="DNA"
      /note="M-Zdhis"
      /organism="artificial sequences"

<400> SEQUENCE: 55
ggtaccacgc gtcttgtaca gctcg                                         25

<210> SEQ ID NO 56
<211> LENGTH: 23
<212> TYPE: PRT
<213> ORGANISM: Tospovirus
<220> FEATURE:
<221> NAME/KEY: SOURCE
<222> LOCATION: 1..23
<223> OTHER INFORMATION: /mol_type="protein"
      /organism="Tospovirus"

<400> SEQUENCE: 56

Val Arg Lys Pro Asn Gly Lys Asn Thr Gly Cys Lys Phe Thr Met His
1               5                   10                  15

Asn Gln Ile Phe Asn Pro Asn
            20

<210> SEQ ID NO 57
<211> LENGTH: 717
<212> TYPE: DNA
<213> ORGANISM: Dermatophagoides pteronyssinus
<220> FEATURE:
<221> NAME/KEY: source
<222> LOCATION: 1..717
<223> OTHER INFORMATION: /mol_type="DNA"
      /organism="Dermatophagoides pteronyssinus"
<220> FEATURE:
<221> NAME/KEY: gene
<222> LOCATION: 1..384
<223> OTHER INFORMATION: /gene="Dp2"
<220> FEATURE:
<221> NAME/KEY: gene
<222> LOCATION: 385..716
<223> OTHER INFORMATION: /gene="Dp5"

<400> SEQUENCE: 57
atggcagatc aagtcgatgt caaagattgt gccaatcatg aaatcaaaaa agttttggta    60
ccaggatgct gtatcattca tcgtggtaaa ccattccaat ggaagccgt tttcgaagcc    120 aaccaaaaca caaaaaccgc taaaattgaa atcaaagcct caatcgatgg tttagaagtt    180
gatgttcccg gtatcgatcc aaatgcatgc cattacatga atgcccatt ggttaaagga    240 caacaatatg atattaaata tacatggaat gttccgaaaa ttgcaccaaa atctgaaaat    300
gttgtcgtca ctgttaaagt tatgcgtgat gatggtgttt tggcctgtgc tattgctact    360
catgctaaaa tccgcggtga agataaaaaa catgattatc aaaatgaatt tgatttctta    420
ttgatggaac gtattcatga acaaattaaa aaaggtgaac ttgcattgtt ctatcttcaa    480
gaacagatta atcattttga agaaaaagcg acaaaagaaa tgaagataa aattgtagcc    540 gaaatggata ccattattgc tatgatcgat ggtgtacgtg gtgtacttga tcgtcttatg    600
caacgtaaag atttagatat ttttgaacaa tataatcttg aaatggctaa aaatctggt    660 gatattttgg aacgtgattt gaaaaagaa gaagcacgtg ttaaaaagat tgaagtt       717
```

EUKARYOTIC EXPRESSION SYSTEM AND USE THEREOF

BACKGROUND OF THE INVENTION

1. Field of the Invention

The present invention relates to an expression system, particularly to a eukaryotic expression system. The present invention also relates to the method of using eukaryotic expression system.

2. Description of the Prior Arts

Dr. Shyi-Dong Yeh's laboratory has disclosed in U.S. Pat. No. 7,718,849 a method for providing resistance to tospovirus by introduction of the highly conserved region of RNA replicase of tospovirus. Transgenic plant with the highly conserved region of RNA replicase from Watermelon silver mottle virus (WSMoV) is produced to be resistant to at least five strains of tospovirus. NSscon (23 aa), a common epitope in the gene silencing suppressor NSs proteins of the members of the WSMoV, was previously identified. In U.S. Pat. No. 7,732,132, monoclonal antibody (MAb) against NSscon is prepared from hybridoma cells deposited with Deposited NO. CCTCC accession number 200718 at China Center for Type Culture Collection (CCTCC), an International Depository Authority. The MAb has proved to have high affinity to NSscon (98-VRKPNGKNTGCKFTMHNQIFNPN-120) (SEQ ID NO. 56). However, the minimal fragment of the NSs protein recognized by said MAb is unknown. The efficacy of the peptide derived from the NSs protein to be used for tagging protein is undefined.

According to the previous description, the current techniques lack a protein tag system with high sensitivity and stability, especially for eukaryotic expression system. To overcome the shortcomings, the present invention provides an expression system with an efficient tag derived from the common epitope of tospoviral NSs proteins to mitigate or obviate the current problems.

SUMMARY OF THE INVENTION

The objective of the present invention is to provide an efficient tag derived from the common epitope of tospoviral NSs proteins for tagging recombinant proteins in eukaryotic expression systems.

The present invention provides a eukaryotic expression system. The eukaryotic expression system comprises a recombinant plant cell. The recombinant plant cell includes a first vector and a second vector. The first vector expresses a fusion protein containing an Asia tospoviral common epitope. The fusion protein containing Asia tospoviral common epitope consists of an amino acid sequence as set forth in SEQ ID NO. 1, and a predetermined protein fragment connecting to the Asia tospoviral common epitope. The second vector expresses a target protein. The target protein interacts with the predetermined protein fragment.

According to the present invention, the fusion protein is steadily expressed in the plant cells. Preferably, the Asia tospoviral common epitope connects to the N-terminus of the predetermined protein fragment, whereas the expression level of the fusion protein is prominently accumulated.

According to the present invention, the predetermined protein is any of known proteins, by expressing known protein tagged with the Asia tospoviral common epitope, the interaction between the predetermined protein fragment and the target protein expressed by the second vector is accessed to monitor the interaction between eukaryotic proteins, such as interaction between potyviral coat protein (CP) and helper component-protease (HC-Pro).

Therefore, in another aspect, the present invention also provides a system for monitoring interaction between eukaryotic proteins, which comprises a recombinant plant cell and a serum or an antibody.

The recombinant plant cell includes a first vector. The first vector expresses a fusion protein containing an Asia tospoviral common epitope.

The fusion protein containing an Asia tospoviral common epitope includes an Asia tospoviral common epitope and a predetermined protein fragment. The Asia tospoviral common epitope consists of an amino acid sequence as set forth in SEQ ID NO. 1. The predetermined protein fragment connecting to the Asia tospoviral common epitope.

The second vector expresses a target protein. The target protein interacts with the predetermined protein fragment; the serum or the antibody is specifically binds to the Asia tospoviral common epitope.

According to the present invention, the serum or antibody against the Asia tospoviral common epitope is coupled with a magnetic bead.

In one another aspect, the present invention provides a method for monitoring the interaction between the eukaryotic proteins. The method in accordance with the present invention comprises the steps of:

providing a plant cell, providing a first vector which expresses a fusion protein containing an Asia tospoviral common epitope, wherein the fusion protein containing Asia tospoviral common has:
  an Asia tospoviral common epitope consisting of an amino acid sequence as set forth in SEQ ID NO. 1, and
  a predetermined protein fragment connecting to the Asia tospoviral common epitope, providing a second vector which expresses a target protein, wherein the target protein interacts with the predetermined protein fragment, and coinfiltrating the first vector and the second vector into the plant cell.

According to the present invention, the step of coinfiltrating the first vector and the second vector into the plant cell includes: preparing recombinant *Agrobacterium tumefaciens* containing the first vector and the second vector respectively, and coinfiltrating the recombinant *Agrobacterium tumefaciens* containing the first vector and the second vector into the plant cell, whereby the fusion protein containing the Asia tospoviral common epitope and the target protein are expressed.

According to the present invention, the plant cell is derived from the group consisting of *Nicotiana benthamiana*, *Solanum lycopersicum* (tomato), *Cucurbitaceae* sp. (melon) and *Citrullus lanatus* (watermelon).

Based on the previous description, the predetermined protein tagged with the Asia tospoviral common epitope is introduced into a eukaryotic cell, such as *Nicotiana benthamiana* cells, and the tagged predetermined protein is detected without affecting the function of the predetermined protein. The system or method utilizes the characteristics of the Asia tospoviral common epitope as a protein tag and via known processes such as co-immunoprecipitation, to assure the interaction between the predetermined protein and the target protein. Therefore, the system and the method in accordance with the present invention are useful for application in plant expression systems.

Other objectives, advantages and novel features of the invention will become more apparent from the following detailed description when taken in conjunction with the accompanying drawings.

BRIEF DESCRIPTION OF THE DRAWINGS

FIG. 1A to FIG. 1C illustrate immunodetection of the minimal length of the tospoviral common epitope NSscon for tagging bacteria-expressed GFP, wherein:

FIG. 1A illustrates construction of the full-length NSscon fused at the C-extreme of GFP in pET28 to form pET28-GFPNSscon-his for expression in the bacterial system, wherein GFP also carried a His-Tag® following the constructed NSscon, T7p indicates the T7 promotor and T7t indicates the T7 terminator;

FIG. 1B illustrates progressive amino acid deletions of NSscon, either from N terminal or C terminal end, for determining the minimal length for its immunorecognition in Western blotting using NSscon MAb and GFP antiserum, wherein NSscon indicates the full length tospoviral common epitope (Chen et al., 2006); the "dn" or "dc" indicates progressive amino acid deletions from N- or C-terminus of NSscon; the numbers of deleted amino acids are indicated;

FIG. 1C illustrates construction of the different tags fused at either N-extreme or C-extreme of GFP and detection of tagged GFPs by Western blotting, wherein FIG. 1C-1 shows construction of the different tags fused at either N-extreme or C-extreme of GFP with full length NSscon, the minimal length NSscon (nss) or polyhistidine (his) sequence in a modified pETsa vector; and FIG. 1C-2 shows detection of tagged GFPs by Western blotting using NSscon MAb, His-Tag® MAb or GFP antiserum;

FIGS. 2A to 2B illustrate results of application of the nss-tag in the bacterial and Zucchini yellow mosaic virus vector expression system, wherein FIGS. 2A-1 to -4 show various proteins were expressed in the bacterial vector system, including NIa protease of Papaya ringspot virus W type (WNpro) (FIG. 2A-1), HC-Pro of Zucchini yellow mosaic virus (ZHC) (FIG. 2A-2), house dust mite chimeric allergen (Dp25) (FIG. 2A-3) and nucleocapsid protein of Watermelon silver mottle virus (WNP) (FIG. 2A-4) by Western blotting; wherein NI indicates the non-induction bacterial fraction; for avoiding the self-proteolysis of HC-Pro, the six a. a of HC-Pro cleavage site (YRVG/G) inadvertently introduced at its C-extreme was removed to retain the tag sequence (ZHCd6nss and ZHCd6his);

FIGS. 2B-1 to 2B-3 illustrate the expression of various proteins in viral vector system, wherein expression levels of GFP, WNP and Dp25 proteins expressed from ZYMV vector system were determined by Western blotting; and protein with His-Tag® was used as control;

FIG. 3A and FIG. 3B illustrate detection of bacterially expressed (FIG. 3A) and Zucchini yellow mosaic virus vector-expressed (FIG. 3B) nss-tagged GFP and nss-tagged WSMoV NP by indirect ELISA using NSscon MAb; wherein the statistical analysis of the reaction of NSscon MAb was performed by ANOVA, meaning a, a' were in a group and have no significant differences, same as to b, b';

DETAILED DESCRIPTION OF THE PREFERRED EMBODIMENTS

In the following examples, nss-tag is proved to be feasible to be applied to monitor recombinant protein expressed by Zucchini yellow mosaic virus vector. Nss-tag is useful for western blotting or enzyme-linked absorption assay (ELISA) to detect recombinant protein. When nss-tagged ZYMV HC-Pro and WSMoV NP are transiently expressed by agroinfiltration in tobacco, they are readily detectable and the tag's possible efficacy for gene silencing suppression is not noticed. Co-immunoprecipitation of nss-tagged and non-tagged proteins expressed confirms the interaction of potyviral HC-Pro and coat protein. Thus, the present invention provides a novel nss-tag system for tagging recombinant protein in both bacterial and plant expression systems.

Example 1

Determination and Applicability of the Minimal Sequence of NSscon in Prokaryotic Protein Expression System In the present example, the NSscon sequence was used for tagging GFP expressed by PET28b vector. The feasibility of NSscon sequence as an epitope tag was tested, and the minimal length of the NSscon sequence recognizable by the NSscon monoclonal antibody (MAb) (Chen et al., 2006, Phytopathology 96, 1296-1304) was determined in the bacterial expression system. All the primers used in this example were listed in Table 1. The green fluorescent protein (GFP) open reading frame (ORF) containing the NSscon sequence (GFP-NSscon), BamHI, KpnI and XhoI sites at its C-extreme was constructed by three successive PCR (35 cycles: 30 s denaturation at 94° C.; 30 s annealing at 55° C.; 2 min synthesis at 72° C.; followed by a 10 min final extension at 72° C.) using the forward primer P-CACC-GFP coupled with three reverse primers, M-NSsconG1-BK, M-NSsconG2 and MNSscon. The GFPNSscon was introduced into pET28b (Novagen, Darmstadt, Germany) via NcoI and XhoI restriction sites to generate pET28-GFPNSscon-his.

TABLE 1 primer for construction of pET28-GFPNSscon-his

| primer name | sequence/SEQ ID NO. | restriction enzyme* |
|---|---|---|
| P-CACC-GFP | 5'-CA<u>CCATGG</u>TGAGCAAGGGCGAGGAGCT-3' (SEQ ID NO. 2) | NcoI |
| M-NSsconG1BK | 5'-GTTCTTCACACCTGGTTTCCTTAC<u>GGTAC CGGATCC</u>CTTGTACAGCTCGTCCATGCCG-3' (SEQ ID NO. 3) | BamHI and KpnI |
| M-NSsconG2 | 5'-TTGATTGTGCATTGTGAACTTGCAGCCT GTGTTCTTCACACCTGGTTTC-3' (SEQ ID NO. 4) | |
| M-NSscon | 5'-GGTG<u>CTCGAG</u>ATTTGGATTAAAGATTTG ATTGTGCATTGTGAA-3' (SEQ ID NO. 5) | XhoI |

*restriction site is underlined.
The stop codon is in bold.

Figure 1A:
Figure 1B:
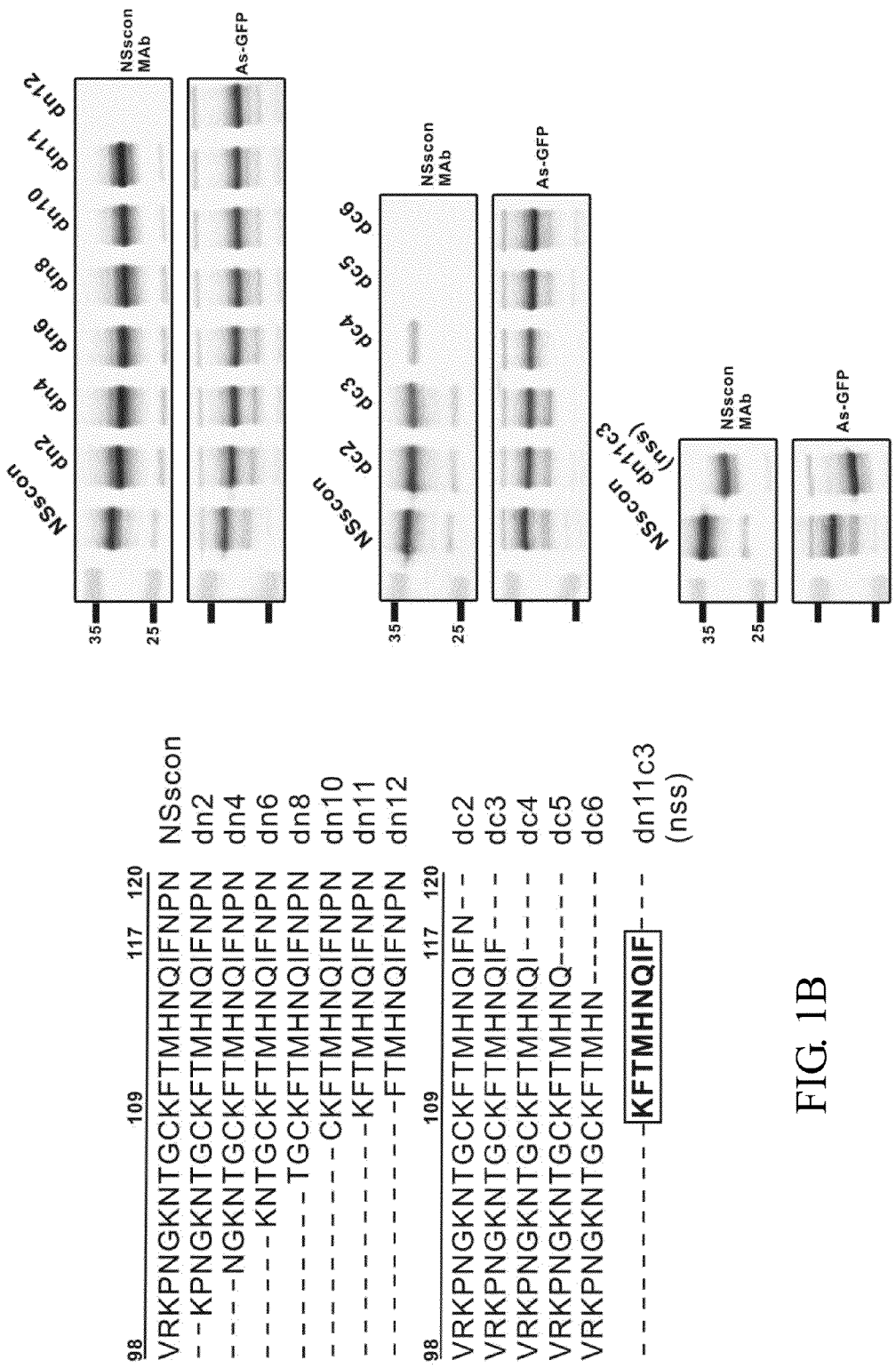

The progressively deleted NSscon, either from its N- or C terminus, were constructed by PCR from pET28-GFPNSscon-his. The primers with added Kpn1, Nco1 or XhoI sites for cloning purpose were listed in Table 2. Individual constructs of GFP fused with different N-terminal deletions (2-12 a. a removed) of NSscon were separately cloned into pET28-GFPNSscon-his via KpnI and XmaI sites (FIG. 1A and FIG. 1B); similarly, those with different C-terminal deletions of NSscon (2-6 a. a removed) were separately cloned into pET28-GFPNSscon-his via NcoI I and XhoI sites (FIG. 1A and FIG. 1B). The GFP fused with the deletion form NSscon 11 a. a deleted from its N-terminal and 3 a. a from C-terminal ends (dn11c3) was constructed by PCR from the pET28-GFP-dn11 using primers P-CACC-GFP and M-NSscon-d3, and then introduced into pET28-GFPNSscon-his by NcoI and XhoI digestion (FIG. 1A and FIG. 1B). All the resulted recombinant plasmids were verified by sequencing.

TABLE 2

Construction of different deletions of NSscon sequence

| primer name | sequence/SEQ ID NO. | restriction enzyme |
|---|---|---|
| Primer for construction of NSscon with N-terminal deletion | | |
| M-pET28-XmaI | 5'-GCATGGTTACTCACCACTGCG-3' (SEQ ID NO. 6) | |
| P-NSscon-d2 | 5'-GT<u>GGTACC</u>AAACCAGGTGTGAAGAACAC-3' (SEQ ID NO. 7) | KpnI |
| P-NSscon-d4 | 5'-GT<u>GGTACC</u>GGTGTGAAGAACACAGGCTGC-3' (SEQ ID NO. 8) | KpnI |
| P-NSscon-d6 | 5'-GT<u>GGTACC</u>AAGAACACAGGCTGCAAGTTC-3' (SEQ ID NO. 9) | KpnI |
| P-NSscon-d8 | 5'-GT<u>GGTACC</u>ACAGGCTGCAAGTTCACAATG-3' (SEQ ID NO. 10) | KpnI |
| P-NSscon-d10 | 5'-GT<u>GGTACC</u>TGCAAGTTCACAATGCACAAT-3' (SEQ ID NO. 11) | KpnI |
| P-NSscon-d11 | 5'-CGT<u>GGTACC</u>AAGTTCACAATGCACAATCA-3' (SEQ ID NO. 12) | KpnI |
| P-NSscon-d12 | 5'-CGT<u>GGTACC</u>TTCACAATGCACAATCAAAT-3' (SEQ ID NO. 13) | KpnI |
| primer for construction of NSscon with C-terminal deletion | | |
| P-CACC-GFP | 5'-CA<u>CCATGG</u>TGAGCAAGGGCGAGGAGCT-3' (SEQ ID NO. 14) | NcoI |
| M-NSscon-d2 | 5'-TG<u>CTCGAG</u>ATTAAAGATTTGATTGTGCATT-3' (SEQ ID NO. 15) | XhoI |
| M-NSscon-d3 | 5'-TG<u>CTCGAG</u>AAAGATTTGATTGTGCATTGTG-3' (SEQ ID NO. 16) | XhoI |

TABLE 2-continued

| Construction of different deletions of NSscon sequence | | |
|---|---|---|
| primer name | sequence/SEQ ID NO. | restriction enzyme |
| M-NSscon-d4 | 5'-TGCTCGAGGATTTGATTGTGCATTGTGAA-3' (SEQ ID NO. 17) | XhoI |
| M-NSscon-d5 | 5'-TGCTCGAGTTGATTGTGCATTGTGAACTT-3' (SEQ ID NO. 18) | |
| M-NSscon-d6 | 5'-TGCTCGAGATTGTGCATTGTGAACTTGCA-3' (SEQ ID NO. 19) | XhoI |

*restriction site is underlined.

The NSscon sequence (23 a. a; residues 98-120 of NSs protein) (SEQ ID NO. 56) was used for tagging GFP expressed by the pET28b vector in bacteria (FIG. 1A and FIG. 1B). The GFP-NSscon containing both the NSscon sequence and His-Tag® was readily detected by Western blotting using NSscon MAb or GFP antiserum (FIG. 1B). GFP tagged with different N-terminal deletions of NSscon (FIG. 1B) were expressed and monitored by Western blotting using NSscon MAb. The NSscon MAb readily recognized the deletion forms of NSscon with up to 11 a. a removed from the N-terminal end, but failed to recognize the 12 a. a-deleted NSscon (FIG. 1B). Our results established that the amino acid residues upstream of K109 of NSscon are dispensable for recognition by the MAb, whereas residue K109 is indispensable. The MAb also recognized the NSscon sequences having 2, 3 and 4 residues deleted from the C-terminal end, but failed to recognize the peptide when 5 or 6 residues were removed (FIG. 1B). These results indicated that residue F117 at the C-terminal region of NSscon is important for MAb recognition, as the reactivity was greatly diminished upon its deletion. Thus, the nine amino acid stretch "109KFTMHNQIF117" (SEQ ID NO: 1) of the NSscon (FIG. 1B) is the minimal length for its recognition by the NSscon MAb; this minimal peptide was designated as "nss" Asia tospoviral common epitope. Serial constructs were generated on a modified pETsa vector to express NSscon-, nss- or his-tagged GFP to compare the detectability of different tags (FIG. 1C). The recombinant GFPs carrying the different tags, either at the N or C-terminus, were monitored by Western blotting using NSscon MAb, His-Tag® MAb (Invitrogen, Carlsbad, USA) or GFP antiserum. Expression of the recombinant GFPs was verified by GFP antiserum and quantified relatively to the untagged GFP. The expression level of GFP tagged with either the whole NSscon or the minimal nss at the N-extreme was higher than that for untagged GFP (FIG. 1C). However, expression levels were lower when either of these tags was individually fused at the C-terminus of GFP; this was especially noticed for the GFP-NSscon fusion (FIG. 1C). Importantly, the expression levels of NSscon- or nss-tagged GFP were comparable to those of his-tagged GFP, indicating that both NSscon and nss can efficiently tag GFP for its expression in the bacterial system. Also, the reaction strength appeared to be similar for NSscon and nss, regardless of their fusion at the N- or C-terminus of GFP.

Example 2

Application of the nss-tag in the Bacterial and Plant Viral Expression System In the present example, construct for recombinant protein with nss-tag was constructed and introduced into a bacterial and plant expression system.

A. Construction of Recombinant Proteins Tagged with NSscon, nss or Poly-Histidine for Expression in Prokaryotic or Eukaryotic Expression System Constructs for recombinant proteins tagged with NSscon, nss or poly-histidine for expression in prokaryotic or eukaryotic expression system were prepared by the step as described as follows.

For using SphI and ApaI restriction sites of primers as cloning sites, pET28b was converted into pET28dsa by abolishing the SphI and ApaI sites of the former by site-directed mutagenesis using the QuikChange™ XL Site-directed mutagenesis Kit (Stratagene, CA, USA). As shown in FIG. 1C, the pETsa-GFP-his carrying GFP ORF with stop codon and pETsa-GFP carrying GFP ORF without stop codon were constructed by PCR amplification of GFP sequence from pET28-GFPNSscon-his using the primer pairs, P-GFP-NSA/M-GFP-BKX and P-GFP-NSA/M-GFP-TGA, respectively, and cloned into the mutated pET28dsa. Primers were listed in Table 3.

TABLE 3

| primers for constructions of construct containing GFP with NSscon, nss or His-tag® in pETsa | | |
|---|---|---|
| primer name | sequence/SEQ ID NO. | restriction enzyme |
| P-del.SphI | 5'-CCGCCGCAAGGAATGGTGCAAGGAGATGGCGCCCAAC-3' (SEQ ID NO. 20) | |
| M-del.SphI | 5'-GTTGGGCGCCATCTCCTTGCACCATTCCTTGCGGCGG-3' (SEQ ID NO. 21) | |
| P-del.ApaI | 5'-GAGACAGAACTTAATGGACCCGCTAACAGC-3' (SEQ ID NO. 22) | |

TABLE 3 -continued primers for constructions of construct containing GFP with NSscon, nss or His-tag® in pETsa

| primer name | sequence/SEQ ID NO. | restriction enzyme |
| --- | --- | --- |
| M-del.ApaI | 5'-GCTGTTAGCGGGTCCATTAAGTTCTGTCTC-3' (SEQ ID NO. 23) | |
| P-GFP-NSA | 5'-GCCATGGCATGCGGGCCCGTGAGCAAGGGCGAGGAGCT-3' (SEQ ID NO. 24) | NcoI, ApaI and SphI |
| M-GFP-BKX | 5'-GGTGCTCGAGGGTACCGGATCCCTTGTACAGCTCGTCCAT-3' (SEQ ID NO. 25) | BamHI, KpnI and XhoI |
| M-GFP-TGA | 5'-GGTGCTCGAGTCAGGTACCGGATCCCTTGTACAGCTCGTCCAT-3' (SEQ ID NO. 26) | BamHI, KpnI and XhoI |
| M-NSsconTGA | 5'-GCCTCGAGTCAATTTGGATTAAAGATTTGATTGTG-3' (SEQ ID NO. 27) | XhoI |
| P-NSscon1 | 5'-TTCACAATGCACAATCAAATCTTTAATCCAAATGCCATGGCATGCGGGCCCGTG-3' (SEQ ID NO. 28) | |
| P-NSscon2 | 5'-GTAAGGAAACCAGGTGTGAAGAACACAGGCTGCAAGTTCACAATGCACAATCA-3' (SEQ ID NO. 29) | |
| P-NSscon | 5'-CACCACATGTCCGTAAGGAAACCAGGTGTGAAG-3' (SEQ ID NO. 30) | PciI |
| P-Cnss | 5'-CAATCAAATCTTTTGAGATCCGGCTGCTAACAAA-3' (SEQ ID NO. 31) | |
| M-Cnss | 5'-TGCATTGTGAACTTCTCGAGGGTACCGGATCCCTTG-3' (SEQ ID NO. 32) | |
| P-Nnss | 5'-ACAATCAAATCTTTCATGCGGGCCCGTGAGCAAGG-3' (SEQ ID NO. 33) | |
| M-Nnss | 5'-GCATTGTGAACTTCACCATGGTATATCTCCTTCTTA-3' (SEQ ID NO. 34) | |
| P-Nhis | 5'-CACCACCACCATGCGGGCCCGTGAGCAAGG-3' (SEQ ID NO. 35) | |
| M-Nhis | 5'-GTGATGGTGCATGGTATATCTCCTTCTTAAAG-3' (SEQ ID NO. 36) | |

*restriction site is underlined.
The stop codon is in bold.

Figures 1, 1C:
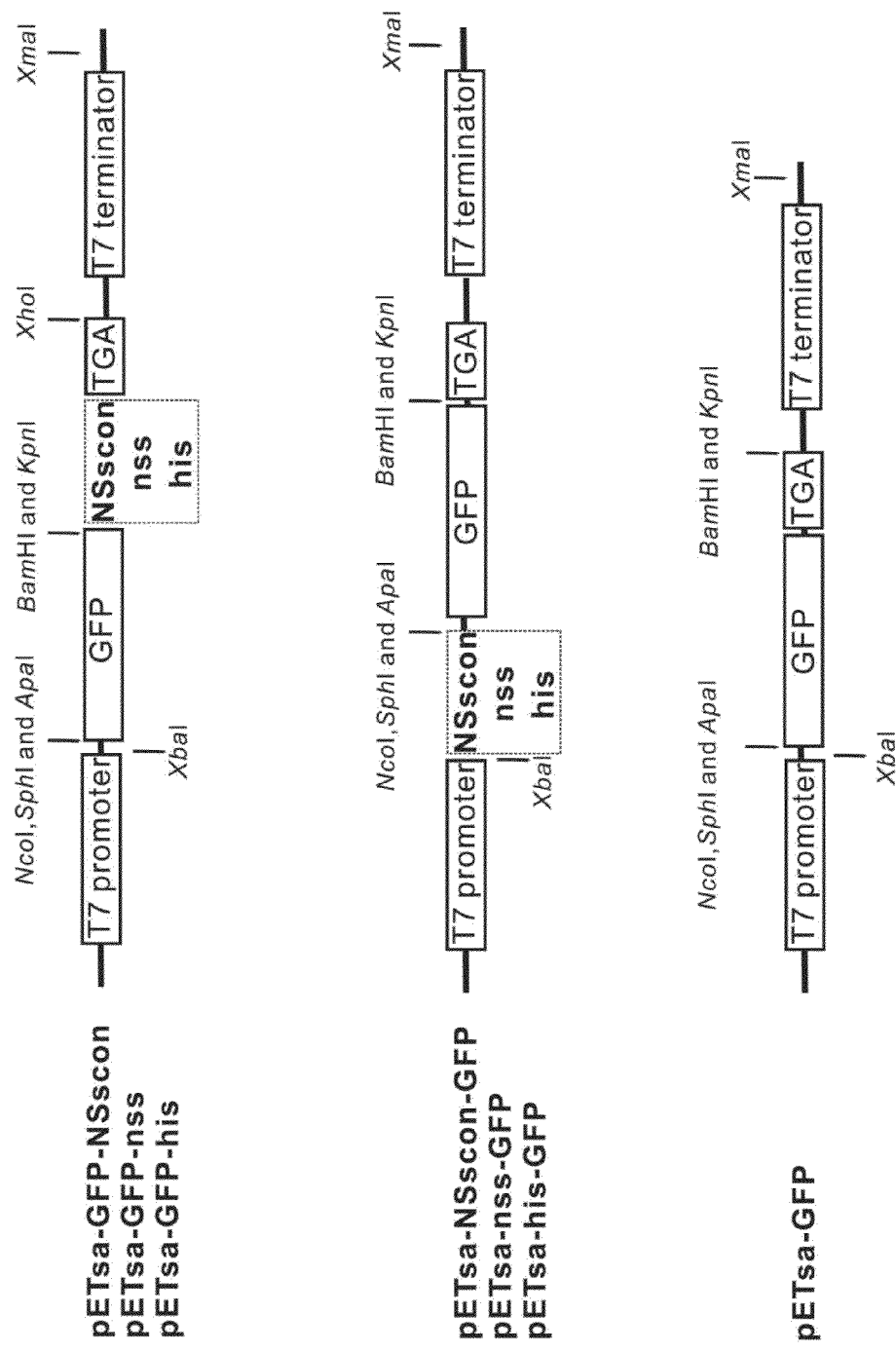
Figures 1, 1C, 2:
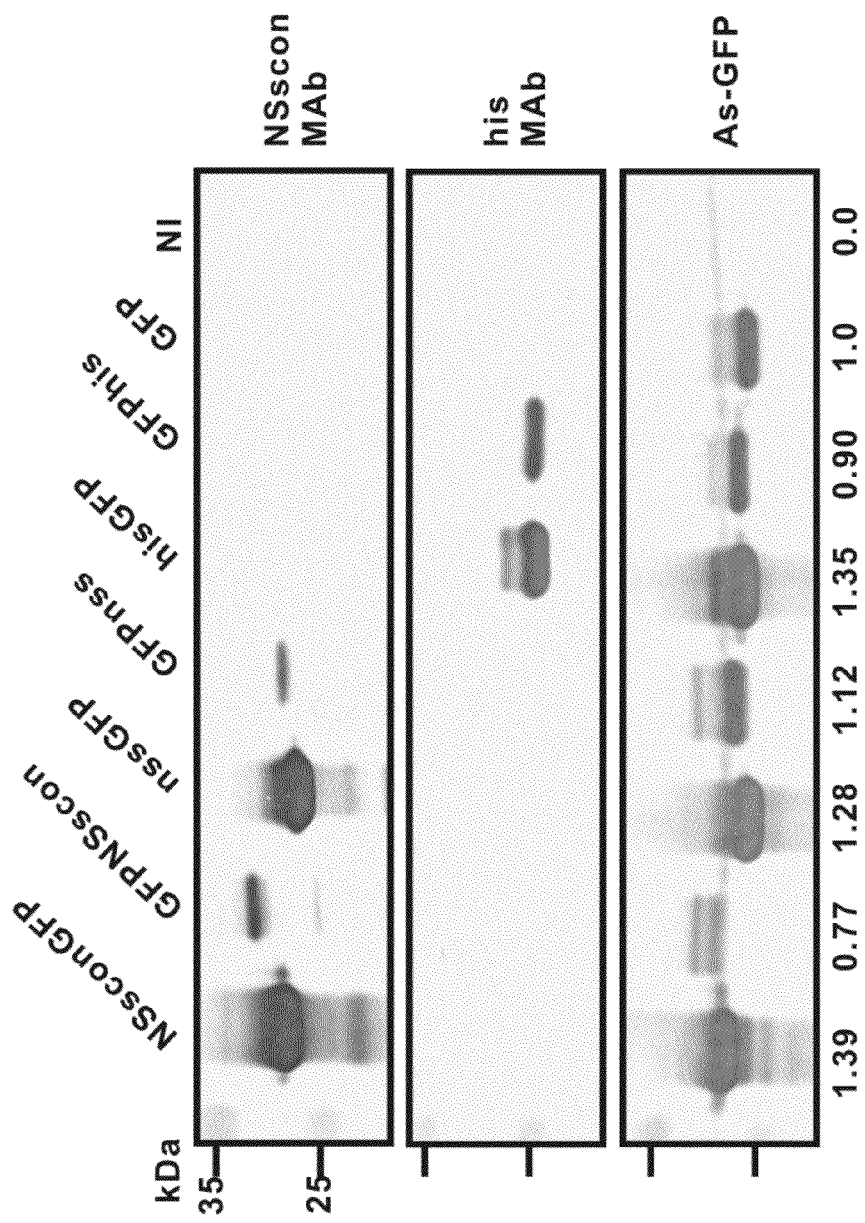

In order to compare the efficiencies of different tags, GFP was individually tagged with NSscon, nss-tag and His-Tag® and the sequences were cloned in bacterial expression vector pET28dsa. The GFP ORF fused with NSscon sequence and stop codon at C terminal end was amplified by PCR using the primers P-GFP-NSA and M-NSsconTGA, and cloned into pETsa-GFP-his via NcoI and XhoI sites to form pETsa-GFP-NSscon (FIG. 1C). The vector pETsa-NSscon-GFP (FIG. 1C) carrying GFP ORF with NSscon sequence at its N-extreme was constructed from pET28-GFPNSscon-his by three successive PCRs using three forward primers, P-NSscon1, P-NSscon2 and P-NSscon, coupled with the reverse primer M-GFPTGA-X. The amplified fragment was cloned into pETsa-GFP via NcoI and XhoI sites.

pETsa-GFP-nss (FIG. 1C) carrying GFP ORF with nss sequence and a stop codon at its C-extreme was constructed pETsa-GFP by a modified site-directed mutagenesis PCR (Stratagene, CA, USA) using the primers P-Cnss and M-Cnss. The pETsa-nss-GFP or pETsa-his-GFP carrying GFP with the nss sequence or His-Tag® at the N-extreme was constructed following the design for pETsa-GFP-nss, using primer pairs P-Nnss/M-Nnss and P-Nhis/M-Nhis, respectively. For tagging other proteins with nss-tag, the ORFs of the NIa protease of Papaya ringspot virus W type (WNpro) (Chen et al., 2008, Molecular Plant-Microbe Interactions 21, 1046-1057), the helper component-protease (HC-Pro) of Zucchini yellow mosaic virus (ZHC) (Lin et al., 2007, Phytopathology 97, 287-296), a chimeric house dust mite allergen, which combined partial Dp2 (384 b. p) and Dp5 (342 b. p) ORFs (Dp25) (SEQ ID NO. 57), and the nucleocapsid protein of Watermelon silver mottle virus (WNP) (Chen et al., 2005, Journal of Virolugical Methods 129, 113-124) were amplified from respective constructs using specific primer pairs (Table 4).

PCR using the primer pair P-nss-d6/M-ZHCd6 or P-his-d6/M-ZHCd6 to generate pETsa-ZHCd6-nss or pET-ZHCd6-his.

From the ZYMV vector p35ZGFPhis, which expresses C terminally his-tagged GFP in cucurbit plants (Hsu et al., 2004), p35ZGFPnss was generated by site-directed mutagen-

TABLE 4 primers for construction of construct containing proteins with various nss-tags in bacterial expression system

| primer name | sequence/SEQ ID NO. | restriction enzyme |
| --- | --- | --- |
| P-WNpro | 5'-CC<u>GCATGC</u>GGAAAAAGTCTTTGCCAAGGCA-3' (SEQ ID NO. 37) | SphI |
| M-WNpro | 5'-CA<u>GCATGC</u>TTGTTCAAAAACATTCAATTGAT-3' (SEQ ID NO. 38) | KpnI |
| P-ZHC | 5'-CA<u>GCATGC</u>TCGTCGCAACCGGAAGTTCAGTTCT-3' (SEQ ID NO. 39) | SphI |
| M-ZHC | 5'-CA<u>GGATCC</u>GCCAACTCTGTAATGCTTCATCTCGCT-3' (SEQ ID NO. 40) | BamHI |
| P-Dp25 | 5'-GC<u>GGGCCC</u>GATCAAGTCGATGTCAAAGATTGT-3' (SEQ ID NO. 41) | ApaI |
| M-Dp25 | 5'-CA<u>GGATCC</u>AACTTCAATCTTTTTAACACGTGCT-3' (SEQ ID NO. 42) | BamHI |
| P-WNP | 5'-CC<u>GCATGC</u>ATGTCTAACGTTAAGCAGCTCACAGA-3' (SEQ ID NO. 43) | SphI |
| P-WNP | 5'-CA<u>GGTACC</u>CACTTCCAAAGAAGTGCTGGGCTT-3'\ (SEQ ID NO. 44) | KpnI |
| P-nss-d6 | 5'-AAGTTCACAATGCACAATCAAATCTT-3' (SEQ ID NO. 45) | |
| P-his-d6 | 5'-CACCACCACCACCACCACTGA-3' (SEQ ID NO. 46) | |
| M-ZHC-d6 | 5'-CATCTCGCTCTGTAGATCATTTGAG-3' (SEQ ID NO. 47) | |
| P-ZCP | 5'-CC<u>GCATGC</u>TCAGGCACTCAGCCAACTGC-3' (SEQ ID NO. 48) | SphI |
| M-ZCP | 5'-CA<u>GCATGC</u>CTGCATTGTGTTCACACCTAA-3' (SEQ ID NO. 49) | KpnI |

* restriction site is underlined

These amplified fragments were individually introduced into the pETsa vector via suitable restriction sites (FIG. 1C). Since the above manipulation, which introduced an inadvertent stretch of nucleotide encoding the HC-Pro cleavable amino acid stretch YRVG/G, led to unintended post-translational removal of the tags from HC-Pro, pETsa-ZHC-nss or pETsa-ZHC-his were modified by site-directed mutagenesis esis PCR using the primer pair P-ZGn/M-ZGn. To express N-terminally his-tagged GFP, p35ZnssGFP was generated from p35ZGFPhis by two successive site-directed mutagenesis with the primer pairs P-ZnG/M-ZnG that added the nss sequence at the N-extreme of GFP and PZdhis/M-Zdhis that deleted the his-tag from p35ZGFPhis. Primers were listed in Table 5).

TABLE 5 primers for construction of construct expressing proteins with nss-tag in ZYMV

| primer name | sequence/SEQ ID NO. |
| --- | --- |
| P-ZGn | 5'-CACAATCAAATCTTTCTCGAGTCCGTACGGCTCCAGTC-3' (SEQ ID NO. 50) |
| M-ZGn | 5'-CATTGTGAACTTGGTACCACGCGTCTTGTACAG-3' (SEQ ID NO. 51) |

TABLE 5-continued primers for construction of construct expressing proteins
with nss-tag in ZYMV

| primer name | sequence/SEQ ID NO. |
|---|---|
| P-ZnG | 5'-CAATCAAATCTTTGCCGGCGCATGCGGGCCCGTGAG-3' (SEQ ID NO. 52) |
| M-ZnG | 5'-TGCATTGTGAACTTACCCATGGTCGACGAATAGT-3' (SEQ ID NO. 53) |
| P-Zdhis | 5'-CTCGAGTCCGTACGGCTCCAGTCATCCA-3' (SEQ ID NO. 54) |
| M-Zdhis | 5'-GGTACCACGCGTCTTGTACAGCTCG-3' (SEQ ID NO. 55) |

The GFP ORFS in p35ZnssGFP and pZGFPnss were replaced by the ORFs of WSMoV NP (Chen et al., 2005) via SphI/KpnI sites or the chimeric Dp25 ORF via ApaI/BamHI sites to generate p35ZnssWNP, p35ZWNPnss, p35ZnssDp25 and p35ZDp25nss, respectively. In order to monitor the transient expression of nss-tagged recombinant proteins by agroinfiltration, the sequences of ZYMV HC-Pro, WSMoV NP and GFP with the nss-tag (either at N- or C-extreme) or without tag were released from pETsa vector and cloned into the binary pBA vector (Niu et al., 2006, Nature Biotechnology 24, 1420-1428) via NcoI/XhoI sites to generate the pBA-nss-ZHC, pBA-ZHC-nss, pBA-ZHC, pBAnss-WNP, pBA-WNP-nss, pBA-WNP or pBA-GFP.

B. Protein Expression and Detection by Western Blotting or Indirect ELISA

In the present example, protein expression and detection were conducted by western blotting or indirect ELISA by the steps as described as follows.

The plasmids for protein expression were transferred into E. coli BL21 cells (Novagen, Darmstadt, Germany); protein expression was performed as described in the manual of pET system (Novagen, Darmstadt, Germany). The plasmids of ZYMV vector were introduced into the systemic host zucchini squash (Cucurbita pepo L. var. Zucchi) by particle bombardment (Hsu et al., 2004). Bacterial protein and ZYMV-infected tissue samples prepared following standard method were separated on a 12% polyacrylamide gel containing sodium dodecyl sulfate. The resolved protein profiles were electro-blotted onto a nitrocellulose membrane using a Bio-Rad® Trans-Blot® apparatus (Trans-Blot® Transfer medium, Bio-Rad, Hercules, Calif.) and the expressed proteins were separately detected using the NSscon monoclonal antibody (MAb) (10,000× dilution) (Chen et al., 2006), GFP antiserum (5000× dilution) (Hsu et al., 2004), PRSV NIa-Pro antiserum (prepared against bacteria-expressed NIa-Pro in our laboratory, unpublished) (5000× dilution), ZYMV HC-Pro antiserum (Wu et al., 2010, Molecular Plant-Microbe Interactions 23, 17-28) (5000× dilution), Dp5 antiserum (Hsu et al., 2004) (5000× dilution) or WSMoV NP MAb (Lin et al., 2005, Phytopathology 95, 1482-1488) (10,000× dilution), following standard procedure. The ZYMV-expressed recombinant proteins were also monitored similarly using the same antisera. The signals were quantified relatively to the untagged proteins by Kodak® 1D image analysis software (Eastman Kodak, Rochester, N.Y.). The feasibility of nss-tagged proteins for detection by indirect enzyme-linked immunosorbent assay (ELISA) was examined. The ELISA analysis of nss-tagged GFP and WSMoV NP expressed in bacterial and ZYMV viral vector systems were done with the NSscon MAb (Chen et al., 2006), GFP antiserum (Hsu et al., 2004) WSMoV NP MAb (Lin et al., 2005, Phytopathology 95, 1482-1488), as described earlier by Yeh and Gonsalves (Yeh and Gonsalves, 1984, Phytopathology 74, 1273-1278).

Figures 1, 2A:
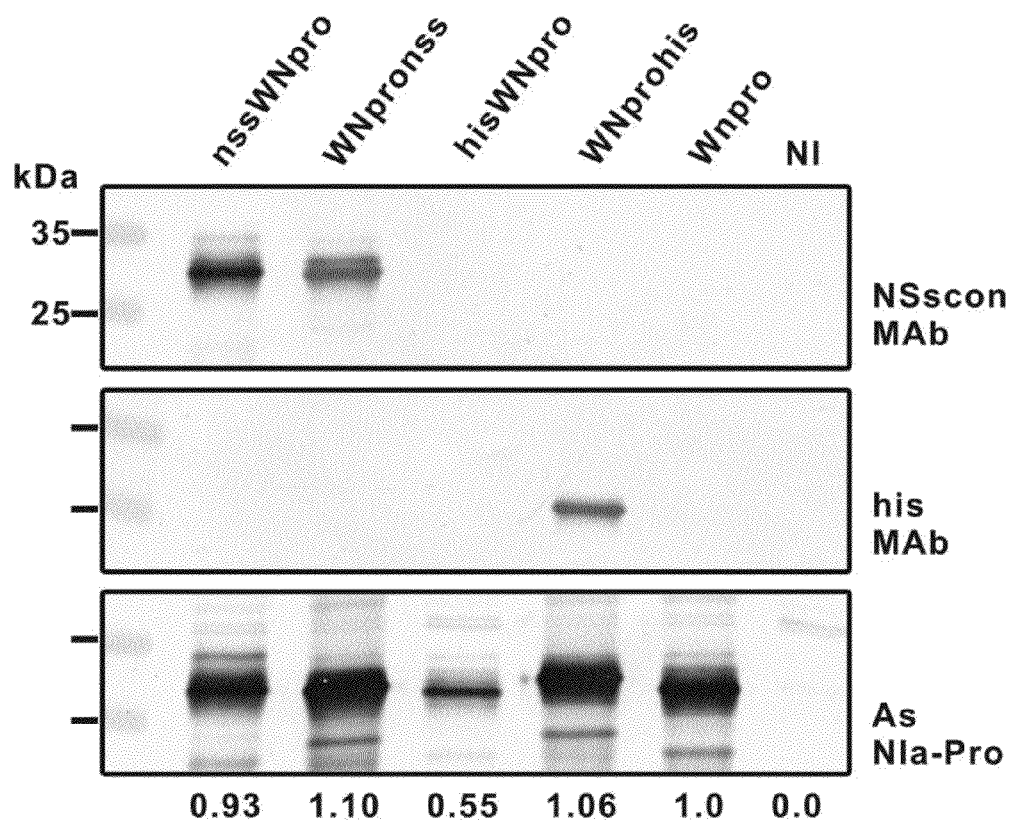
Figures 2, 2A:
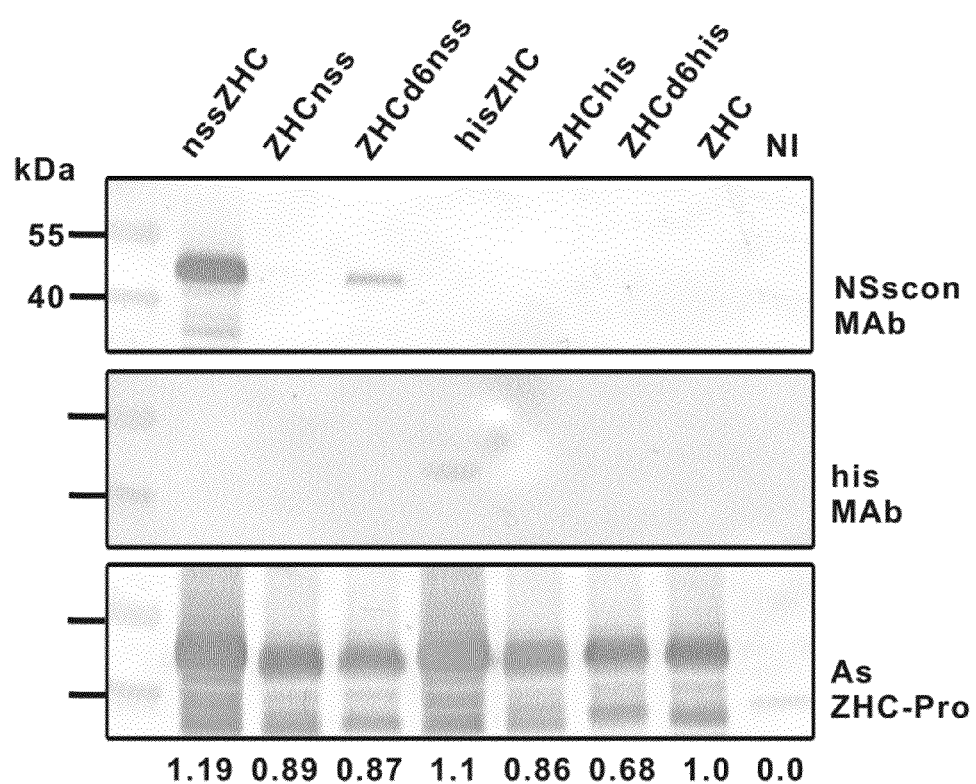
Figures 2, 2A, 3:
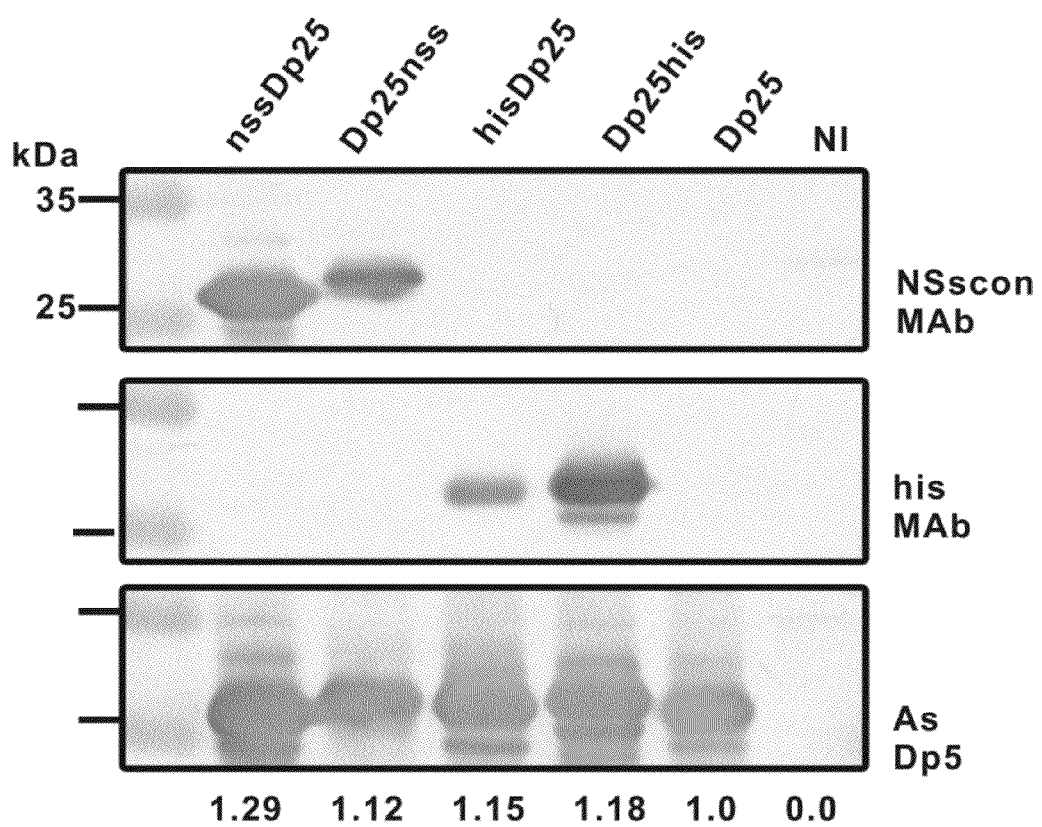
Figure 3A:
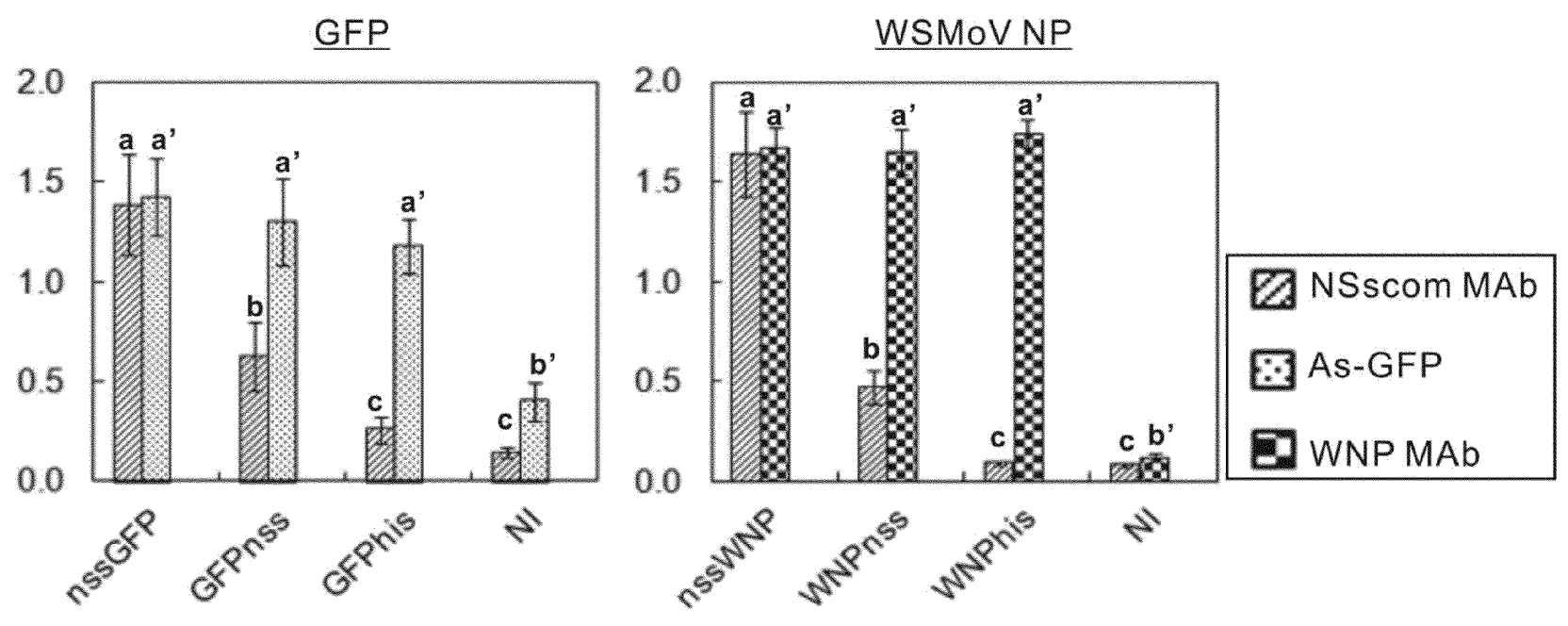
Figure 3B:
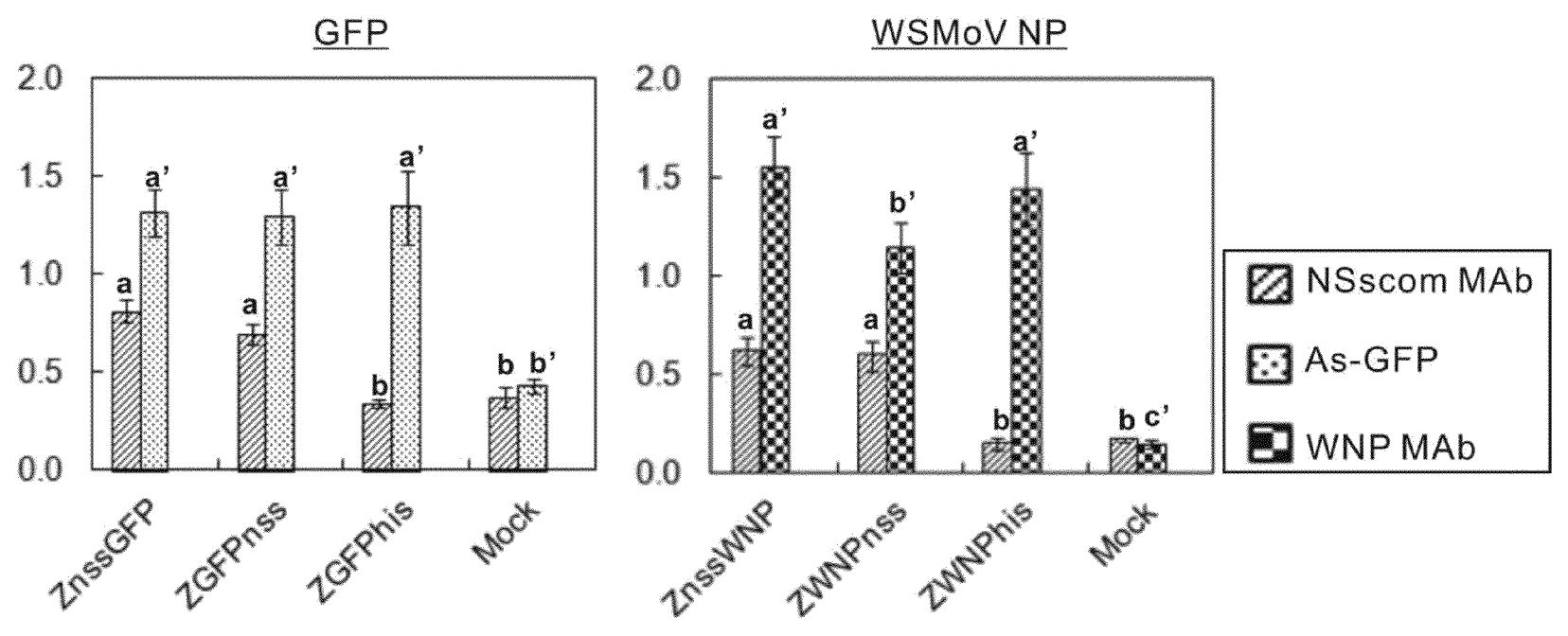

In the present example, the results demonstrated that the four test proteins fused were detected by the NSscon MAb, except for the HC-Pro-nss fusion (FIG. 2A). This isolated failure was understood to be because of an HC-Pro cleavage site (YRVG/G) inadvertently introduced during the construction, which allowed an autocatalytic cleavage by HC-Pro (Carrington et al., 1989) that removed the tag following translation. Restoration of detection of nss-tag was accomplished by deletion of the cleavage site from the C-terminal region of HC-Pro (FIG. 2A, ZHCd6nss); however, the His-Tag® was still not detected (FIG. 3B, ZHCd6his). Expression levels of all recombinant proteins were similar, as shown by Western blot assays using the individual antibodies against each protein (FIG. 2A). WNpro and WNP with His-Tag® at their N-termini and ZHC-Pro with His-Tag® at its C-terminus were not detected, while his-tagged Dp25 at its N-terminus was barely detected. When an equal amount of 5 μg purified IgG was used for comparison, the nss-tagged GPFs were detected at 256× antigen dilution by NSscon MAb, comparable to the detection sensitivity of the protein by GFP antiserum but superior to the detectability of the His-Tag® MAb which only detected his-tagged GFP up to 32× dilution (data not shown). These results indicated that the nss-tag has greater detection sensitivity for recombinant proteins than the His-Tag®.

Figures 1, 2B:
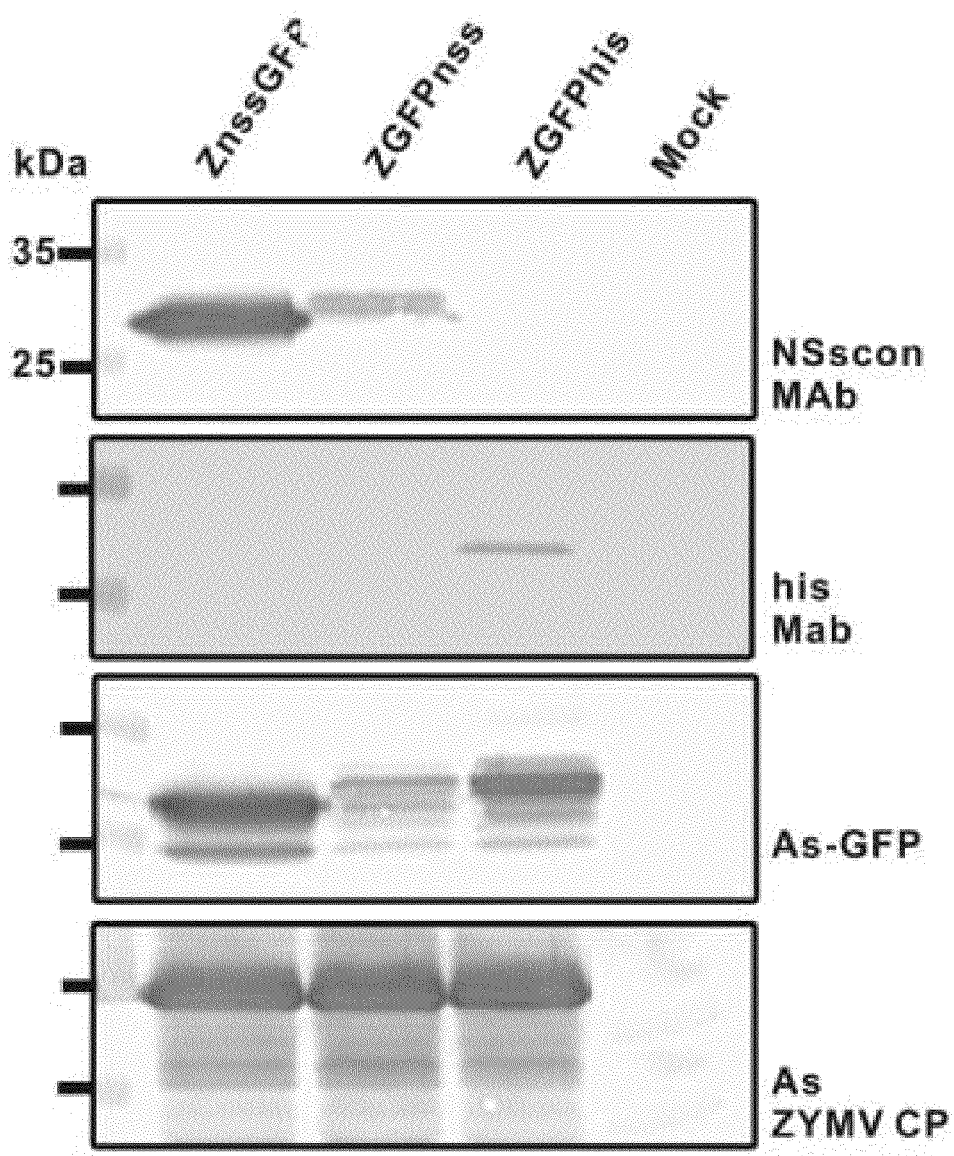

The above results demonstrate that all the recombinant viruses were infectious and the nss-tagged recombinant proteins were detected by NSscon MAb by Western blotting from squash plants (FIGS. 2B and 3B). The nss-tagged GFP and WNP expressed by bacterial or ZYMV vector system were also readily detected by ELISA using NSscon MAb.

Overall, the results indicate that the recombinant proteins tagged with the nss sequence can be readily detected by the NSscon MAb, regardless of the nss-tagged terminus and that the nss sequence is suitable to be used as an epitope tag in both bacterial and plant viral vector expression systems.

Example 3

The Effect of nss-tag on Functions of Tagged Proteins

Since the nss sequence is derived from the common epitope of the tospoviral PTGS suppressor, NSs protein (Takeda et al., 2002, FEBS Letters 532, 75-79), in the present example examined was the possibility for nss-tag's functional interference with the tagged ZYMV HC-Pro, a gene silencing suppressor, and WSMoV NP, a non-gene silencing suppressor. The nss-tagged and non-tagged ZYMV HC-Pro and WSMoV NP were separately constructed in a binary vector and expressed in leaves of *N. benthamiana* by agroinfiltration.

In order to monitor the transient expression of nss-tagged recombinant proteins in plants by agroinfiltration, the sequences of ZYMV HC-Pro, WSMoV NP and GFP fused with the nss sequence (either at N- or C-extreme) or without tag were released from pETsa vector and cloned into the binary pBA vector (Niu et al., 2006, Nature Biotechnology 24, 1420-1428) via NcoI/XhoI sites to generate the pBA-nss-ZHC, pBA-ZHC-nss, pBAZHC, pBA-nss-WNP, pBA-WNP-nss, pBA-WNP or pBA-GFP. These binary vectors were introduced into *Agrobacterium tumefaciens* ABI strain by electroporation and cultured in Luria-Bertani medium (LB) with Kanamycin and spectinomycin at 28.0 overnight. The cells were pelleted down and resuspended to an OD600 of 1.0 in 10 mM $MgCl_2$ containing 0.015 mM acentonsyrigone and kept in room temperature for 3 hours. Suspensions of *A. tumefaciens* ABI carrying pBAGFP (a GFP expressor, driven constitutively by a 35 S promoter), pBAGFi (a 2/3 GFP ORF construct with inverted repeat and used as a silencing inducer, provided by Dr Shih-Shun Lin, National Taiwan University, Taiwan) were mixed with individual constructed vectors (ratio 1:1:1) and then injected into the lower side of leaves *Nicotiana benthamiana* Domin plants of 10 cm height stage by a syringe without needle and the plants were kept at 25° C. The empty vector pBA (Niu et al., 2006) was used as a negative control. The transiently expressed recombinant proteins at 3 dpi were monitored by chemiluminescent Western blotting (Amersham, Bucks, U.K.) using ZYMV HC-Pro antiserum (Wu et al., 2010, Molecular Plant-Microbe Interactions 23, 17-28), WSMoV NP MAb (Lin et al., 2005, Phytopathology 95, 1482-1488) or NSscon MAb (Chen et al., 2006) as the primary antibody and horseradish peroxidase-conjugated goat anti-rabbit immunoglobulin (Amersham, Bucks, U.K.) or horseradish peroxidase-conjugated goat anti-mouse immunoglobulin (Amersham, Bucks, U.K.) as the secondary antibody. The GFP fluorescence was monitored at 3 dpi by a hand-held UV light B-100AP (UVP, CA, USA) and photographed with a digital camera (D7000™, Nikon, Japan) with a Cokin™ P series filter (Cokin, 84 mm, 524 nm, French).

Figure 4A:
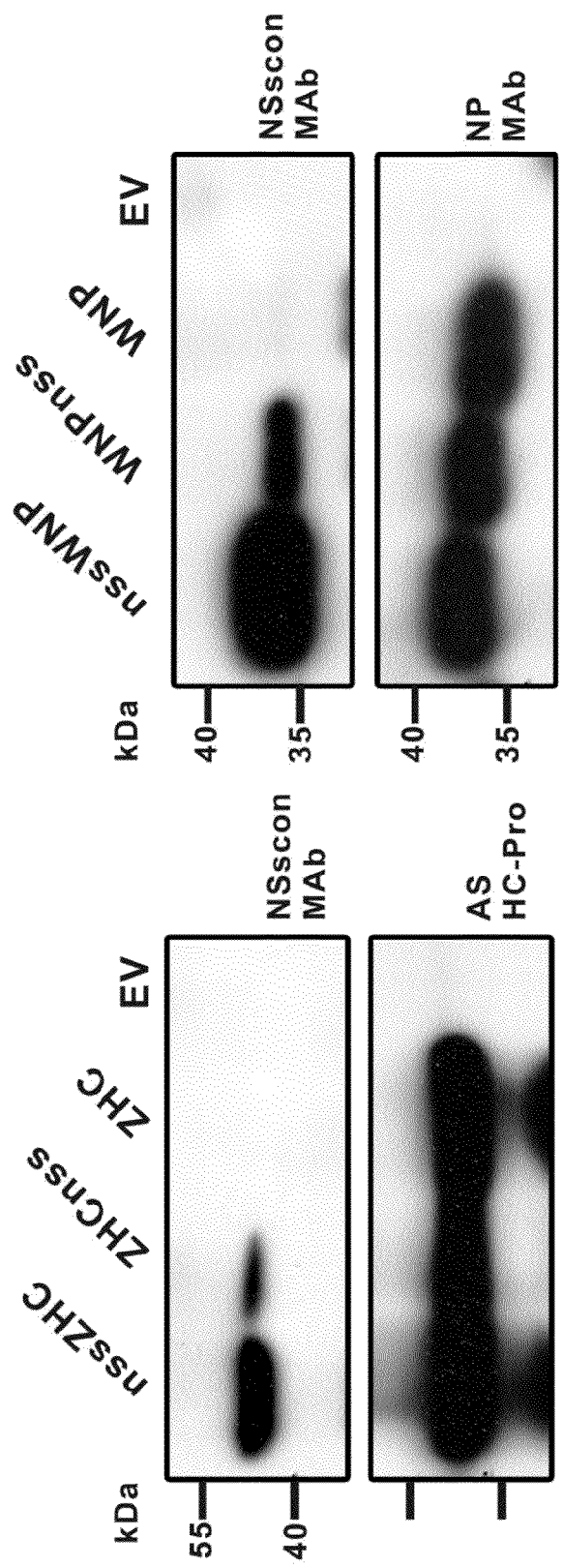
FIG. 4A illustrates detection of tagged ZHCs or WNPs by Western blotting using HC-Pro antiserum, WSMoV NP MAb or NSscon MAb.
Figure 4B:
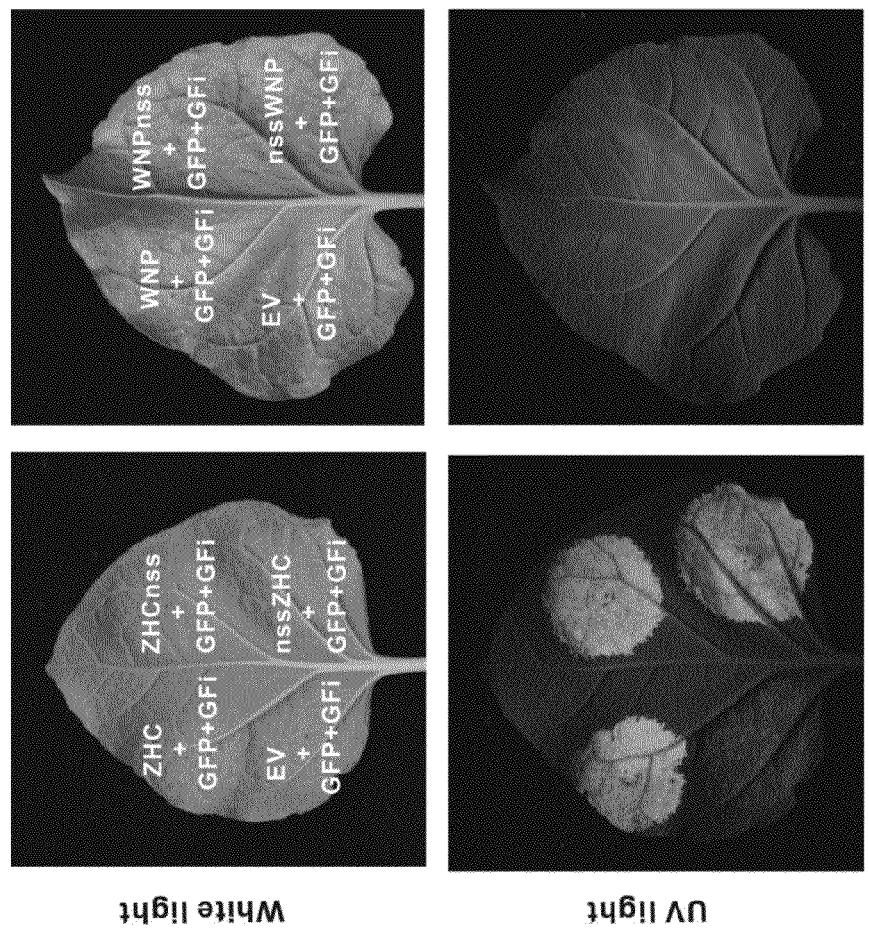
FIG. 4B illustrates suppressor activity assay of ZYMV HC-Pro and WSMoV NP fused with the nss-tag, wherein the GFP expression construct and GFi were coinfiltrated with nss-tagged HC-Pro (a silencing suppressor) or NP proteins (a non-silencing suppressor) on leaf tissues of *Nicotiana bethamiana* to test the suppression of GFP silencing, and the photographs were taken under white light or UV light at 3 dpi. EV indicates the empty vector.

The above results demonstrated that at 3 dpi, recombinant ZYMV HC-Pro tagged with the nss sequence, either at the N- or C-terminus, was readily detected by HC-Pro antiserum and NSscon MAb (FIG. 4A). The nss-tagged forms of WSMoV NP were expressed to similar levels, based on their detection by the NP MAb and NSscon MAb (FIG. 4A). At 3 dpi, GFP expression was completely silenced when coinfiltrated with the GFi silencing inducer (FIG. 4B). In contrast, fluorescent signals of GFP were similar if coinfiltrated with the GFi construct with either the nss-tagged or non-tagged HC-Pro (FIG. 4B). However, GFP expression was not restored if coinfiltrated with the GFi construct with the nss-tagged or non-tagged NP (FIG. 4B). The results indicated that nss-tag renders the tagged transiently expressed recombinant proteins immunodetectable and the tag neither interferes with the suppressor activity of ZYMV HC-Pro, nor confers the function of gene silencing suppression on WSMoV NP.

Example 4

Co-Immunoprecipitation of nss-tagged ZYMV CP or HC-Pro In Vitro

The interaction of potyviral coat protein (CP) and HC-Pro is essential for the aphid transmission of potyviruses (Atreya and Pirone, 1993 Proceedings of the National Academy of Sciences of the United States of America 90, 11919-11923; Granier et al., 1993, Journal of General Virology 74, 2737-2742). In order to test if the nss sequence can be used for co-immunoprecipitation analysis of interacting proteins, in the present example, either the bacteria-expressed nss-tagged ZYMV CP or nss-tagged HC-Pro was treated with the other non-tagged interacting protein and the complex was immunoprecipitated using NSscon MAb.

ZYMV CP with or without nss-tag was first cloned into the pETsa vector (FIG. 1C) by PCR with primers P-ZCP and M-ZCP (Table 4). *E. coli* BL21 cells were transformed with the individual plasmids carrying ZYMV CP (pETsa-nss-ZCP, pETsa-ZCP-nss or pETsa-ZCP). ZYMV HC-Pro sequences with or without the nss-tag (pETsa-nss-ZHC, pETsa-ZHCd6-nss or pETsa-ZHC) were also used for this example. Following induced expression of recombinant proteins, *E. coli* cells were pelleted and resuspended in 1 ml extraction buffer (50 mM Tris-HCl, 150 mM NaCl, 0.5% Triton X-100, 5% glycerol, 1 mM EDTA and 0.02% $NaN_3$) containing protease inhibitor cocktail (Roche Diagnostics, IN, USA), lysed with a sonicator 250-450 Sonifier Analog Cell Disruptor (Branson, Conn., USA) and then centrifuged at 13,000 rpm for 5 minutes. The presence of recombinant proteins in soluble fractions was confirmed with the antiserum against ZYMV CP (Hsu et al., 2004, Journal of Allergy and Clinical Immunology 113, 1079-1085) or HC-Pro (Wu et al., 2010, Molecular Plant-Microbe Interactions 23, 17-28). Aliquots of each 300 µl sample containing nss-tagged HC-Pro or nss-tagged CP were mixed with each 100 µl sample containing non-tagged CP or non tagged HC-Pro (i.e., nssZHC+ZCP; ZHCnss+ZCP or nssZCP+ZHC; ZCPnss+ZHC) and incubated at 4° C. for 1 hour. Purified IgG of NSscon MAb (100 µg, described above) was added to each reaction mixture and incubated at 4° C. for 1 hour. Then 25 µl Mag Protein A Sepharose™ (GE Healthcare Life Sciences, Uppsala, Sweden) was added and the mixture was incubated further for 1 hour. The tubes were kept on a magnetic platform (MagRack6) to capture the Mag Protein A Sepharose™ beads. After washing with 600 µl extraction buffer two times, the beads were resuspended in 100 µl sample buffer and the immunoprecipitated proteins were analyzed by Western blotting using the antiserum against ZYMV HC-Pro or CP to detect the non-tagged protein pulled down by NSscon MAb through co-immunoprecipitation with the nss-tagged proteins.

Figure 5A:
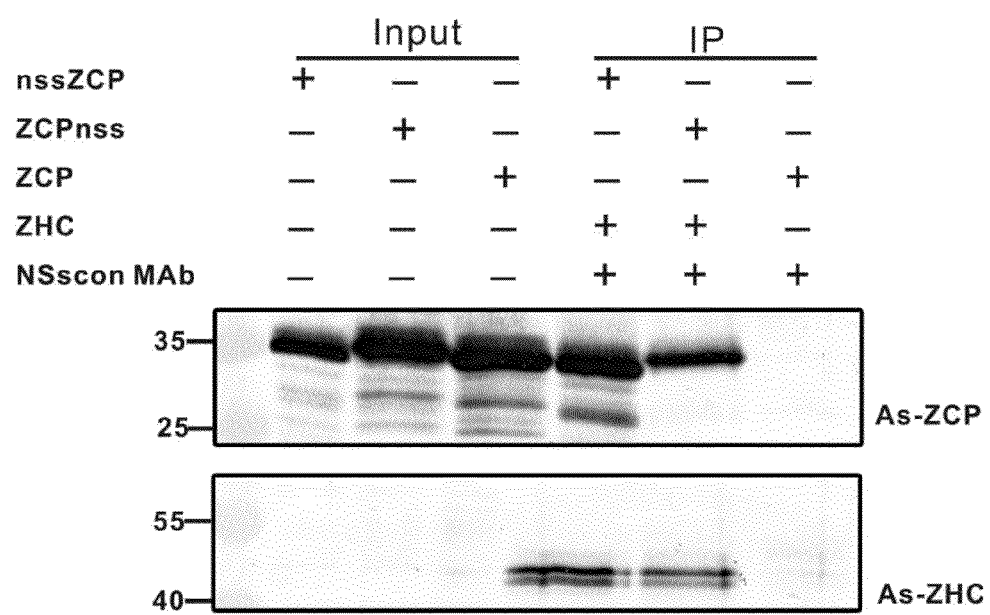
FIG. 5A and FIG. 5B illustrate results of co-immunoprecipitation of nss-tagged Zucchini yellow mosaic virus CP (FIG. 5A) or nss-tagged HC-Pro (FIG. 5B) using NSscon MAb in vitro, wherein "Input" indicates that the solution contained only the nss-tagged CP or nss-tagged HC-Pro; IP" indicates that the NSscon MAb was used to pull down the nss-tagged recombinant proteins from the CP/HC-Pro mixed solutions. The presence of nss-tagged or untagged ZYMV CP and HC-Pro from the "Input" and "IP" fractions was detected by Western blotting using ZYMV CP antiserum (As-ZCP) and HC-Pro antiserum (As-ZHC), respectively.
Figure 5B:
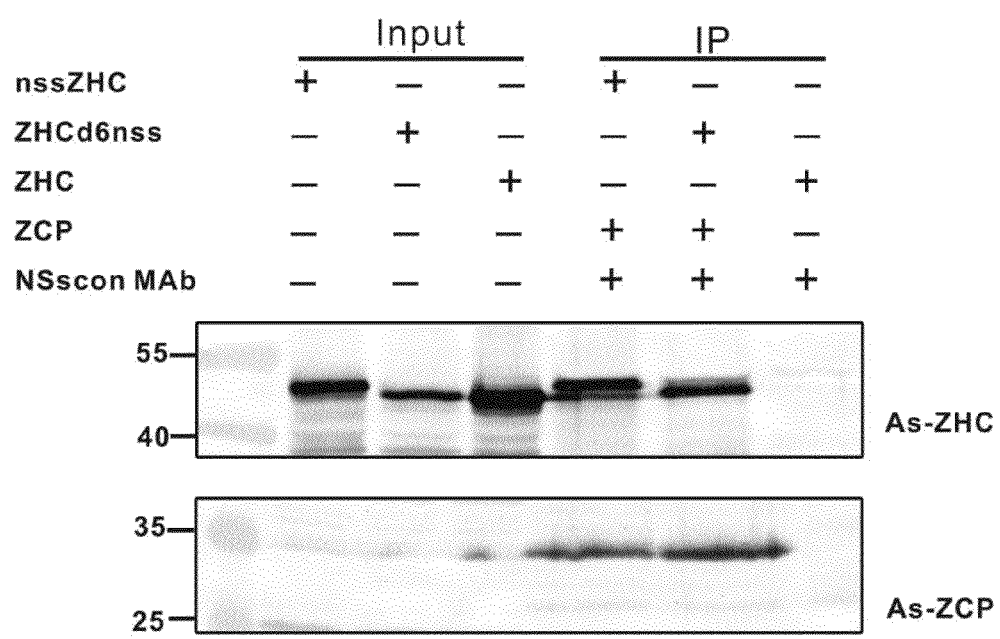

According to the above results, the non-tagged HCPro was co-immunoprecipitated with the nss-tagged CPs (either nssZCP or ZCPnss) by NSscon MAb and was able to be detected by HC-Pro antiserum (FIG. 5A). Similarly, the non-tagged CP was co-immunoprecipitated with nss-tagged HC-Pros (FIG. 5B). Taken together, the results demonstrated the co-immunoprecipitation of non-tagged HC-Pro/CP with nss-tagged CP/HC-Pro, implying that the nss-tag is applicable for co-immunoprecipitation analyses for protein-protein interactions.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A eukaryotic expression system, comprising: a recombinant plant cell that includes:
   1) a first vector that expresses a fusion protein consisting of: a) an Asia tospoviral common epitope consisting of an amino acid sequence as set forth in SEQ ID NO: 1; and b) a predetermined protein fragment of Zucchini yellow mosaic virus coat protein (ZYMV CP), wherein said predetermined protein fragment is connected to said Asia tospoviral common epitope; and
   2) a second vector that expresses a target protein that binds with the predetermined protein fragment, wherein the target protein is ZYMV HC-Pro that binds to said ZYMV CP.

2. The eukaryotic expression system according to claim 1, wherein the Asia tospoviral common epitope connects to the N-terminus of the predetermined protein fragment.

3. The eukaryotic expression system according to claim 2, wherein the first vector comprises a pBA binary vector inserted with a sequence encoding the fusion protein containing the Asia tospoviral common epitope.

4. The eukaryotic expression system according to claim 1, wherein the recombinant plant cell is derived from the group consisting of *Nicotiana benthamiana, Solanum lycopersicum, Cucurbitaceae* sp. and *Citrullus lanatus*.

5. The eukaryotic expression system according to claim 2, wherein the recombinant plant cell is derived from the group consisting of *Nicotiana benthamiana*, tomato, melon and watermelon.

6. The eukaryotic expression system according to claim 3, wherein the recombinant plant cell is derived from the group consisting of *Nicotiana benthamiana*, tomato, melon and watermelon.

7. A system for monitoring binding between proteins, the system comprising:
   a recombinant plant cell including:
   1) a first vector that expresses a fusion protein consisting of: a) an Asia tospoviral common epitope consisting of an amino acid sequence as set forth in SEQ ID NO: 1; and b) a predetermined protein fragment of Zucchini yellow mosaic virus coat protein (ZYMV CP), wherein said predetermined protein fragment is connected to the Asia tospoviral common epitope; and
   2) a second vector that expresses a target protein that binds with said predetermined protein fragment, wherein said target protein is ZYMV HC-Pro that binds to the Zucchini yellow mosaic virus coat protein; and a serum or an antibody against one of the following: the Asia tospoviral common epitope, the target protein, or the predetermined protein fragment.

8. The system for monitoring binding between proteins according to claim 7, wherein the serum or antibody against the Asia tospoviral common epitope is coupled with a magnetic bead.

9. The system for monitoring binding between proteins according to claim 7, wherein the recombinant plant cell is derived from the group consisting of *Nicotiana benthamiana, Solanum lycopersicum, Cucurbitaceae* sp. and *Citrullus lanatus*.

10. A method for expressing proteins in a plant cell, comprising:
    1) providing a plant cell;
    2) providing a first vector that expresses a fusion protein consisting of: an Asia tospoviral common epitope consisting of an amino acid sequence as set forth in SEQ ID NO: 1; and a predetermined protein fragment of Zucchini yellow mosaic virus coat protein (ZYMV CP), wherein said predetermined protein fragment is connected to said Asia tospoviral common epitope;
    3) providing a second vector which expresses a target protein, wherein the target protein binds with the predetermined protein fragment of Zucchini yellow mosaic virus coat protein (ZYMV CP); and
    4) coinfiltrating the first vector and the second vector into the plant cell.

11. The method for expressing proteins in a plant cell according to claim 10, wherein the step of coinfiltrating the first vector and the second vector into the plant cell includes: preparing recombinant *Agrobacterium tumefaciens* containing the first vector and the second vector respectively; and coinfiltrating the recombinant *Agrobacterium tumefaciens* containing the first vector and the second vector into the plant cell, whereby the fusion protein containing the Asia tospoviral common epitope and the target protein are expressed.

12. The method for expressing proteins in a plant cell according to claim 10, wherein the plant cell is derived from the group consisting of *Nicotiana benthamiana, Solanum lycopersicum, Cucurbitaceae* sp. and *Citrullus lanatus*.

* * * * *